(12) United States Patent
Rodes et al.

(10) Patent No.: US 9,304,117 B2
(45) Date of Patent: Apr. 5, 2016

(54) AEROSOL EXPOSURE MONITORING

(71) Applicant: Research Triangle Institute, Research Triangle Park, NC (US)

(72) Inventors: Charles E. Rodes, Cary, NC (US); J. Randall Newsome, Apex, NC (US)

(73) Assignee: Research Triangle Institute, Durham, NC (US)

( * ) Notice: Subject to any disclaimer, the term of this patent is extended or adjusted under 35 U.S.C. 154(b) by 29 days.

(21) Appl. No.: 14/354,426

(22) PCT Filed: Oct. 26, 2012

(86) PCT No.: PCT/US2012/062167
§ 371 (c)(1),
(2) Date: Apr. 25, 2014

(87) PCT Pub. No.: WO2013/063426
PCT Pub. Date: May 2, 2013

(65) Prior Publication Data
US 2014/0347663 A1 Nov. 27, 2014

Related U.S. Application Data

(60) Provisional application No. 61/551,660, filed on Oct. 26, 2011.

(51) Int. Cl.
*G01N 33/00* (2006.01)
*G01N 21/53* (2006.01)
*G01N 1/22* (2006.01)
(Continued)

(52) U.S. Cl.
CPC .......... *G01N 33/0027* (2013.01); *G01N 1/2273* (2013.01); *G01N 15/0255* (2013.01); *G01N 21/51* (2013.01); *G01N 21/53* (2013.01); *G01N 33/0016* (2013.01)

(58) Field of Classification Search
USPC ................... 356/335–343, 436–437; 73/23.2, 73/863.22, 53.01, 28.05, 863.03
See application file for complete search history.

(56) References Cited

U.S. PATENT DOCUMENTS 4,940,327 A * 7/1990 Lilienfeld .......... G01N 15/0205
356/338
4,942,297 A 7/1990 Johnson et al.
(Continued)

FOREIGN PATENT DOCUMENTS

WO 99/41588 A1 8/1999
WO 2013/063426 A2 5/2013

OTHER PUBLICATIONS

International Search Report and Written Opinion dated Apr. 22, 2013 for corresponding Int'l. Patent Appl. No. PCT/US2012/062167.

*Primary Examiner* — Sang Nguyen
(74) *Attorney, Agent, or Firm* — David P. Gloekler; Olive Law Group, PLLC

(57) ABSTRACT

A gas processing device such as an aerosol exposure monitor is configured for acquiring chronic data, acute data, or both simultaneously, and may include a pump and a noise dampening device. The noise dampening device may include an elastomeric membrane between an inlet chamber and an outlet chamber. In another aspect, an aerosol exposure monitor may include an impactor, a collection filter, and a nephelometer that includes a sample chamber integrated with an aerosol flow path associated with the impactor and collection filter.

15 Claims, 16 Drawing Sheets

Figure 1:
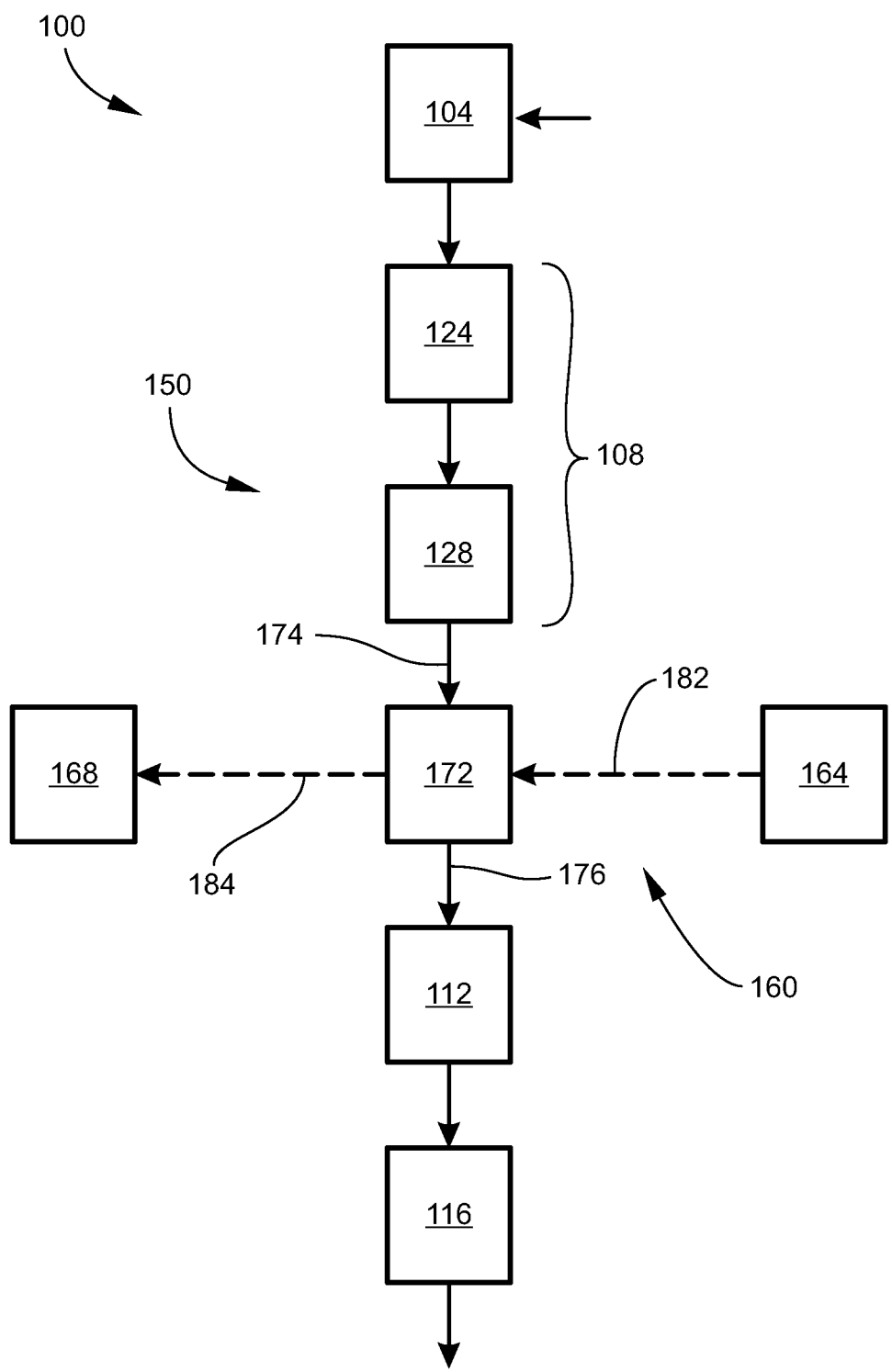

(51) Int. Cl.
*G01N 15/02* (2006.01)
*G01N 21/51* (2006.01)

(56) References Cited

U.S. PATENT DOCUMENTS

| | | | |
|---|---|---|---|
| 5,090,233 A | 2/1992 | Kogure et al. | |
| 5,425,802 A * | 6/1995 | Burton | B01D 45/08 209/143 |
| 5,659,388 A * | 8/1997 | Scheer | G01N 15/065 356/37 |
| 5,932,818 A | 8/1999 | Novick et al. | |
| 6,431,014 B1 * | 8/2002 | Liu | G01N 1/2208 73/28.05 |
| 2003/0223063 A1 * | 12/2003 | Hill | G01N 21/64 356/340 |
| 2008/0137065 A1 * | 6/2008 | Oberreit | G01N 30/84 356/37 |
| 2011/0310386 A1 * | 12/2011 | Renard | G01N 15/06 356/340 |
| 2011/0314937 A1 * | 12/2011 | Johnson | G01N 15/0255 73/863.22 |
| 2012/0174650 A1 * | 7/2012 | Ariessohn | B08B 3/12 73/23.2 |

* cited by examiner

```
┌─────────────┐   Strong linear    ┌─────────────┐
│  on board   │ ⇐  Response     ⇒  │   Adult     │
│accelerometer│   (R² = 0.90)      │ Ventilation │
│   output    │                    │Rate (m³/min)│
└─────────────┘                    └─────────────┘
                 ┌─────────────┐
                 │ nephelometer│
                 │ data (µg/m³)│
                 └─────────────┘
                        ⇓
                 Potential dose
       ⇘        (µg/min/kg) from      ⇙
                aerosol concentration
```

Fig. 12

# AEROSOL EXPOSURE MONITORING

RELATED APPLICATIONS

This application is the national stage of International Application No. PCT/US2012/062167, filed Oct. 26, 2012, titled "AEROSOL EXPOSURE MONITORING," which claims the benefit of U.S. Provisional Patent Application Ser. No. 61/551,660, filed Oct. 26, 2011, title "AERO6SOL EXPOSURE MONITORING," the contents of both of which is incorporated by reference herein in their entireties.

STATEMENT REGARDING FEDERALLY SPONSORED RESEARCH OR DEVELOPMENT

This invention was made with government support under contract no. U01 ES016093 awarded by National Institute of Health. The government has certain rights in the invention.

TECHNICAL FIELD

The present invention relates to personal level aerosol exposure monitors and their uses, including aerosol exposure monitors that are portable, and personal level aerosol exposure monitors that are wearable by a user resulting from an inherently low burden design, for simultaneous personal exposure monitoring applying both real time and integrated filter analyses.

BACKGROUND

An aerosol exposure sensor and sampler is utilized to sample the aerosol in the immediate vicinity of the aerosol exposure monitor to enable the breathing zone aerosol particles to be analyzed by any number of different techniques. The aerosol exposure monitor may be designed for indoor, outdoor, or personal use. A personal exposure monitor is typically designed to be worn by a person to sample the aerosol in that person's breathing zone.

Aerosol sampling may be done over a specified period of time (integration period). The aerosol exposure monitor may be configured to aerodynamically size and then collect particles during the integration period, after which the collected particles are analyzed. As an example, the aerosol exposure monitor may include a sample inlet that leads to a housing that contains a substrate. The substrate, for example a filter, is configured to enable particles of a desired size range to accumulate thereon. At the conclusion of the integration period, the substrate may be removed and subjected to one or more types of destructive or non-destructive analyses. This type of aerosol exposure monitor is useful for enabling the acquisition of chronic or long-term exposure data, but is limited by the fact that it is not able to perform any type of measuring, sensing or detecting function in real time during the integration period. That is, this type of aerosol exposure monitor merely collects a total population of one or more types of particles over the integration period, after which one or more separate analyses must be done to acquire data that may be integrated or averaged over the integration period. This type of aerosol exposure monitor may be passive or active. A passive monitor relies on natural aerosol flow applying convection rather than diffusion to size and collect the aerosol. A passive monitor can be a low-burden (as to size, weight, and quietness) device, with little or no energy requirements, but does not collect them aerodynamically and collects so few particles that analytical techniques such as gravimetric mass analysis are either extremely limited or impossible.

On the other hand, an active monitor includes some type of fluid-moving device (typically a pump) to positively establish a flow of aerosol into the sizer of the active monitor. An active monitor may enable robust particle collections, and also facilitates the inclusion of an aerosol impactor in the active monitor and thus enables aerodynamic sizing of the particles being sampled. An active monitor, however, requires more power than a passive monitor due to the need for operating the pump. In the case of a personal exposure monitor, batteries are utilized to supply power and thus the additional power required for the pump limits the duration of the aerosol sampling period. Moreover, an active monitor is typically burdensome due to the inclusion of the pump, associated plumbing, possibly an aerosol impactor, and in personal applications a battery pack. In addition to being larger and heavier than a passive monitor, the active monitor has conventionally been noisy due to the operation of the pump. The higher burden typically imposed by an active monitor poses a significant wearing compliance problem in the case of personal exposure monitors. In particular, the person to be monitored may be required to wear the active monitor during prescribed intervals of time and during certain activities (which may include exercise or other activities involving a high level of motion and personal exertion) over the course of the sampling period. The acquisition of valid data from the personal exposure monitor thus requires "wearing compliance" by the person. The higher the burden imposed by the active monitor, the less likely wearing compliance will occur. As an example, recent testing of personal monitors has shown that the majority of elementary age children are not comfortable with sensor systems that weigh more than 300 grams and add more than 5 decibels to the environment.

Another type of aerosol exposure monitor may be configured to acquire data from the aerosol being sample in real time during a prescribed sampling period. One example is a nephelometer, which typically measures particles in a fluid stream by illuminating the particles and detecting the resulting light that is scattered from the particles. Unlike a turbidometer, which measures the effects of high concentrations of particles, a nephelometer is designed to measure both low and high concentrations of particles. A nephelometer measures particle concentration in real time and thus would be useful in the context of a personal exposure monitor for acquiring peak exposure data. To be convenient to carry and use, the nephelometer should be as small and compact as possible. The nephelometer should also be highly sensitive to the entire range of concentrations of particles the wearer might encounter.

In view of the foregoing, there is an ongoing need for aerosol exposure monitors that present extremely low burden and thus are useful as personal devices that are easily wearable by users. It would also be useful to provide an aerosol exposure monitor capable of simultaneously acquiring both chronic and acute exposure data. There is also a need for active aerosol exposure monitors capable of operating without excessive noise.

SUMMARY

To address the foregoing problems, in whole or in part, and/or other problems that may have been observed by persons skilled in the art, the present disclosure provides methods, processes, systems, apparatus, instruments, and/or devices, as described by way of example in implementations set forth below.

According to one implementation, an aerosol exposure monitor includes an impactor to size the aerosol; a sample chamber communicating with the impactor and defining a fluid flow path along a first axis; a collection filter communicating with the sample chamber and removable from the aerosol exposure monitor; a pump communicating with the collection filter; a light source; a light detector; a first bore defining a first optical path from the light source to the sample chamber along a second axis; and a second bore defining a second optical path from the sample chamber to the light detector along a third axis, wherein the first axis, the second axis and the third axis are at angles to each other.

In some implementations, the collection filter may be contained in or be part of a cassette that facilitates installation and removal of the collection filter and avoids contamination of the filter material. In some implementations, the first axis, the second axis and the third axis are mutually orthogonal to each other.

According to another implementation, a gas processing device includes a housing; a sample inlet defining a gas flow path into the housing; a pump disposed in the housing and including a pump inlet and a pump outlet; and a noise dampening device disposed in the housing. The noise dampening device includes an inlet chamber interposed between the sample inlet and the pump inlet, an outlet chamber communicating with the pump outlet, and an elastomeric membrane interposed between and fluidly isolating the inlet chamber and the outlet chamber.

In some implementations, the gas processing device is or includes an aerosol exposure monitor, which may include, for example, a particle collection filter and/or a nephelometer.

According to another implementation, a method for monitoring aerosol includes sizing particles of the aerosol by flowing the aerosol through an impactor; collecting the sized particles by flowing the aerosol through a sample chamber along a first axis and through a collection filter, wherein the sized particles are collected on the collection filter, and wherein flowing the aerosol through the impactor, the sample chamber and the collection filter comprises operating a pump communicating with an outlet side of the collection filter; irradiating the sized particles flowing through the sample chamber by directing an irradiating light into the sample chamber along a second axis angled relative to the first axis, wherein scattered light propagates from the irradiated particles; and directing the scattered light to a light detector along a third axis angled relative to the first axis and the second axis to sense a total scattering potential of the sized particles.

According to another implementation, method for monitoring aerosol includes operating a pump to establish a flow of aerosol into a housing and to a collection filter disposed in the housing, wherein aerosol particles of a desired size range are collected on the collection filter and gas from the aerosol flows through the collection filter; flowing the gas from an outlet side of the collection filter, through an inlet chamber, and into an inlet of the pump; and flowing the gas from an outlet of the pump, through an outlet chamber, and through an exhaust port open to a region outside the outlet chamber, wherein the outlet chamber is adjacent to the inlet chamber and an elastomeric membrane is interposed between and fluidly isolates the inlet chamber and the outlet chamber, wherein the gas flowing through the inlet chamber contacts a first side of the elastomeric membrane, and the gas flowing through the outlet chamber simultaneously contacts a second side of the elastomeric membrane, and noise associated with the respective flows of the gas through the inlet chamber and the outlet chamber is reduced.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

FIG. 1 is a schematic view of an example of an aerosol exposure monitor according to an implementation of the present disclosure.

FIG. 2 is a schematic view of an example of a nephelometer according to an implementation of the present disclosure.

FIG. 3 is a schematic view of an example of an aerosol exposure monitor according to another implementation of the present disclosure.

FIG. 4 is a schematic (or functional block) diagram illustrating various signal processing functions that may be implemented by the aerosol exposure monitor illustrated in any of FIGS. 1-3.

FIG. 5 is a perspective view of an example of an aerosol exposure monitor according to another implementation of the present disclosure, with a portion of its housing removed.

FIG. 6 is a top view of an assembly that includes an aerosol collection device and a nephelometer, which may be included with the aerosol exposure monitor illustrated in FIG. 5.

FIG. 7 is a perspective view of the assembly with a portion cut-away along line A-A of FIG. 6.

FIG. 8 is an elevation view of the assembly with the same portion cut-away as in FIG. 7.

FIG. 9 is an exploded view of a noise dampening device, which may be included with the aerosol exposure monitor illustrated in FIG. 5.

FIG. 10 is a perspective view of the noise dampening device illustrated in FIG. 9.

FIG. 11 is a plot of measured sound level (dBA) of the aerosol exposure monitor illustrated in FIGS. 5-10 as a function of the length (cm) of an exhaust tube of the noise dampening device illustrated in FIG. 9, for a flow rate of 0.5 liters/minute.

FIG. 12 is a functional diagram illustrating examples of processes for calculating ventilation rate and potential dose.

FIG. 13 are plots of raw tri-axial (x, y and z values) accelerometer data (in g units) over time (in sec) acquired from an accelerometer-equipped aerosol exposure monitor worn by a person while (A) sitting at a computer, (B) walking at 2 mph on a treadmill, and (C) indoor cycling at 70 RPM.

FIG. 14 is an example of a screenshot generated by software configured to provide an interface with the aerosol exposure monitor.

DETAILED DESCRIPTION

As used herein, the term "aerosol" generally refers to an assembly of liquid or solid particles suspended in a gaseous medium long enough to be observed and measured. The size of aerosol particles typically ranges from about 0.001 μm to about 100 μm. See Kulkarni et al., Aerosol Measurement, $3^{rd}$ ed., John Wiley & Sons, Inc. (2011), p. 821. The term "gaseous fluid" generally refers to a gas (or gaseous fluid, or gas-phase fluid). A gas may or may not contain liquid droplets or vapor, and may or may not contain aerosol particles (or particulates, or particulate matter). An example of a gas is, but is not limited to, ambient air. An aerosol may thus be considered as comprising particles and a gas that entrains or carries the particles. A "gas" may also refer to an aerosol that has been filtered to remove particles from the aerosol. That is, an aerosol may be flowed through a filter designed to remove particles of a certain size range from the gas phase of the aerosol. As a result, the gas flowing from the outlet side of the filter may be substantially free of particles, or at least substantially free of particles of the size range intended to be blocked by the filter. For purposes of the present disclosure, the component of the pre-filtered aerosol that is allowed to pass through a filter will be referred to as a gas. Additionally, the term "fluid" is used herein interchangeably with the term "gas" unless the context dictates otherwise.

FIG. 1 is a schematic view of an example of an aerosol exposure monitor (or monitoring apparatus, or monitoring device) 100 according to an implementation of the present disclosure. The aerosol exposure monitor 100 generally includes an aerosol sample inlet 104, an aerosol sample impactor (or impactor assembly) 108, an aerosol sample collection filter (or filter assembly) 112, and a pump 116. All of the foregoing components may be contained in a suitable housing or enclosure (not shown). The sample inlet 104 is open to the ambient environment outside the aerosol exposure monitor 100. The sample inlet 104 may be configured such that the flow path of aerosol 120 entering the sample inlet 104 is turned at an angle (e.g., ninety degrees) before flowing into the impactor 108. The right angle design smoothly transitions aerosol via a laminar flow regime from the front of the breathing zone of an individual wearing the device into the impactor 108 with minimal internal losses. FIG. 1 schematically depicts the order of succession of the components, with each component being in fluid communication with the preceding component. The aerosol exposure monitor 100 is structurally configured to establish (or define) a fluid flow path (or "gas" flow path) generally running from the sample inlet 104, through the impactor 108, through the collection filter 112, and into the pump 116.

The impactor 108, often termed an aerosol impactor, particle impactor or intertial impactor, may have any configuration suitable for aerodynamically sizing particles in the sample aerosol flow whereby particles of a desired aerosol size range are collected on the collection filter 112. The impactor 108 may be a multi-stage impactor configured for effecting sizing in successive stages, which may provide greater tolerance for high particle concentration by minimizing particle bounce. In the illustrated implementation, the impactor 108 is a dual-stage impactor and hence includes a first impactor stage 124 followed by a second impactor stage 128. The impactor 108 may be configured to minimize the impact of undesirable particle bounce between stages 124, 128 onto the subsequent collection filter 112. The sample inlet 104 and impactor 108 may be configured as an assembly or module that is removable from the aerosol exposure monitor 100 to enable selection of different cut-points, for example $PM_{2.5}$ (particulate matter of 2.5-micron size and smaller), $PM_{10}$ (particulate matter of 10-micron size and smaller), etc. The sample inlet 104 (or an initial stage of the impactor 108) may include a coarse screening inlet (not shown) to prevent entry of large particles, insects, and other unwanted matter. In one example of a dual-stage impactor assembly configured for $PM_{2.5}$, the impactor 108 includes a 10-µm coarse inlet, followed by a 4.0-µm cut-point first impactor stage 124, followed by a 2.5-µm second impactor stage 128. In one example of a dual-stage impactor assembly configured for $PM_{10}$, the impactor 108 includes a 20-µm coarse inlet, followed by a 12-µm cut-point first impactor stage 124, followed by a 10-µm second impactor stage 128. In some implementations, the impactor stages 124, 128 are configured for a cut-point accuracy of +/−0.5 µm.

The collection filter 112 may be any filter suitable for serving as a substrate for collecting particles of the desired size range, and which exhibits a low pressure drop for the flow rates contemplated for the aerosol exposure monitor 100. In some implementations, the rated porosity of the collection filter 112 ranges from 2.0 to 3.0 microns (µm). In a specific example, the nominal porosity of the collection filter 112 is 3 µm. In some implementations, the composition of the collection filter 112 is PTFE (polytetrafluoroethylene) although it will be understood that other materials that are suitably free of background contamination may be suitable. The pressure drop through (across the thickness of) the collection filter 112 should be low enough to avoid exceeding the capacity of the pump 116 and to minimize consumption of battery power. In some implementations, the collection filter 112 is configured such that it exhibits a pressure drop of nominally less than about 5 cm of water (or less than about 2 inches $H_2O$) at a flow rate of 0.5 liters/minute (and typical ambient temperature). In some implementations, the collection filter 112 is configured such that it exhibits a pressure drop of nominally less than about 2.5 cm of water (or about 1 inches $H_2O$ or less) at a flow rate of 0.5 liters/minute (and typical ambient temperature). In one example, the collection filter 112 is a commercially available, 3-µm porosity, 25-mm outside diameter Pall Gelman TEFLO® filter. In some implementations, the collection filter 112 is removable from the aerosol exposure monitor 100. For this purpose, the collection filter 112 may be provided in the form of a filter assembly that includes a filter element (i.e., the actual filter material) held in a filter cartridge. The collection filter 112 may be removed by opening the housing of the aerosol exposure monitor 100 and handling the filter cartridge, employing a tool such as a pair of tweezers if necessary or desired.

The pump 116 may be any small pump or micro-pump suitable for low flow-rate operation, and which does not generate an excessive amount of pulsing. The pump 116 may be configured to operate at a low flow rate that allows the collection filter 112 to collect particles over a significant duration of time, such as a day, a week, or longer. The low flow rate also assists in avoiding turbulent flow along the flow path of the aerosol through the aerosol exposure monitor 100, minimizing the fluid velocity seen at the upstream surface of the collection filter 112 and hence assisting in preventing significant internal losses and overloading of the collection filter 112 when collecting particles over the course of an extended sampling duration. The pump 116 may also be configured to operate continuously over the desired sampling period, or to operate cyclically to reduce consumption of battery power and thus enable an extended sampling period. In some implementations, the pump 116 may be configured to operate at a flow rate ranging from 0.30 to 0.60 lpm (liters per minute). In one specific implementation, the pump 116 operates at a flow rate of 0.5 lpm. In one example, the pump 116 is a rotary vane pump. The pump 116 may generally include pump (or fluid moving) components actuated by a motor. The motor may be in signal communication with circuitry (not shown) configured to control the operation of the pump 116. The pump 116 may exhaust into an interior of the aerosol exposure monitor 100 or to an outlet provided by the housing of the aerosol exposure monitor 100.

The provision of the pump 116 renders the aerosol exposure monitor 100 an active device, requiring electrical power beyond that needed to operate the electronic circuitry and other active components provided with the aerosol exposure monitor 100. The pump 116, however, actively establishes a controlled fluid flow through the aerosol exposure monitor 100, thus facilitating the use of the impactor 108 upstream of the collection filter 112. The low flow rate and optional cyclical operation of the pump 116 minimize the additional power consumed by the aerosol exposure monitor 100. The aerosol exposure monitor 100 may include an AC adapter to enable line power to be supplied from a wall outlet or other external power source, and/or may include a universal serial bus (USB) or other suitable connection to enable power to be supplied from a computing device, and/or may include an interface configured to receive batteries of standard design. In some implementations, the pump 116 and associated circuitry utilize only a small number of batteries, for example three AA-size batteries and optionally a coin-type battery for backup power. In some implementations, the aerosol exposure monitor 100 may be configured for optional connection to an external battery pack to extend the duration of the sampling period.

In operation, the aerosol exposure monitor 100 may be activated manually by the user by pressing an ON button. Optionally, the aerosol exposure monitor 100 may include timing circuitry configured for activating the aerosol exposure monitor 100 automatically according to a predetermined schedule. Optionally, the aerosol exposure monitor 100 may include a wireless transceiver to enable the aerosol exposure monitor 100 to be activated remotely. In all cases, activation/deactivation of the aerosol exposure monitor 100 starts/stops the pump 116. The pump 116 establishes a flow of aerosol from the ambient into the aerosol exposure monitor 100 via the sample inlet 104, and through the aerosol exposure monitor 100 along the flow path described above. Particles of the aerosol are sized by the impactor 108, and the remaining particles are accumulated on the collection filter 112. The period of operation, i.e., the duration of aerosol sampling and concomitant particle collection, may be any specified duration such as, for example, a day, a week, or longer. Once sampling is completed, the aerosol exposure monitor 100 may be deactivated manually or automatically. The collection filter 112 may then be removed from the aerosol exposure monitor 100 and subjected to any desired destructive or non-destructive analysis of the collected particles known to persons skilled in the art or later developed, such as gravimetric analysis, speciation analysis, chemical analysis, spectroscopic or spectrometric analysis, crystallographic analysis, etc. The analysis (or analyses) may entail any qualitative or quantitative determination of interest such as, for example, concentration of particles over time, personal level of exposure to particles, characterization of particles (e.g., size distribution, morphology, composition, toxicity, identification of particles), etc. The removed collection filter 112 may be replaced with a new collection filter 112 and the aerosol exposure monitor 100 may thereafter be re-deployed in subsequent sampling operations. The collection filters 112 utilized in this implementation may be housed in a cassette to minimize contamination from handling. Optionally, the individual impactor surfaces of the respective impactor stages 124, 128 may be removed to enable analysis of the particle sizes captured by the impactor surfaces.

Figure 2:
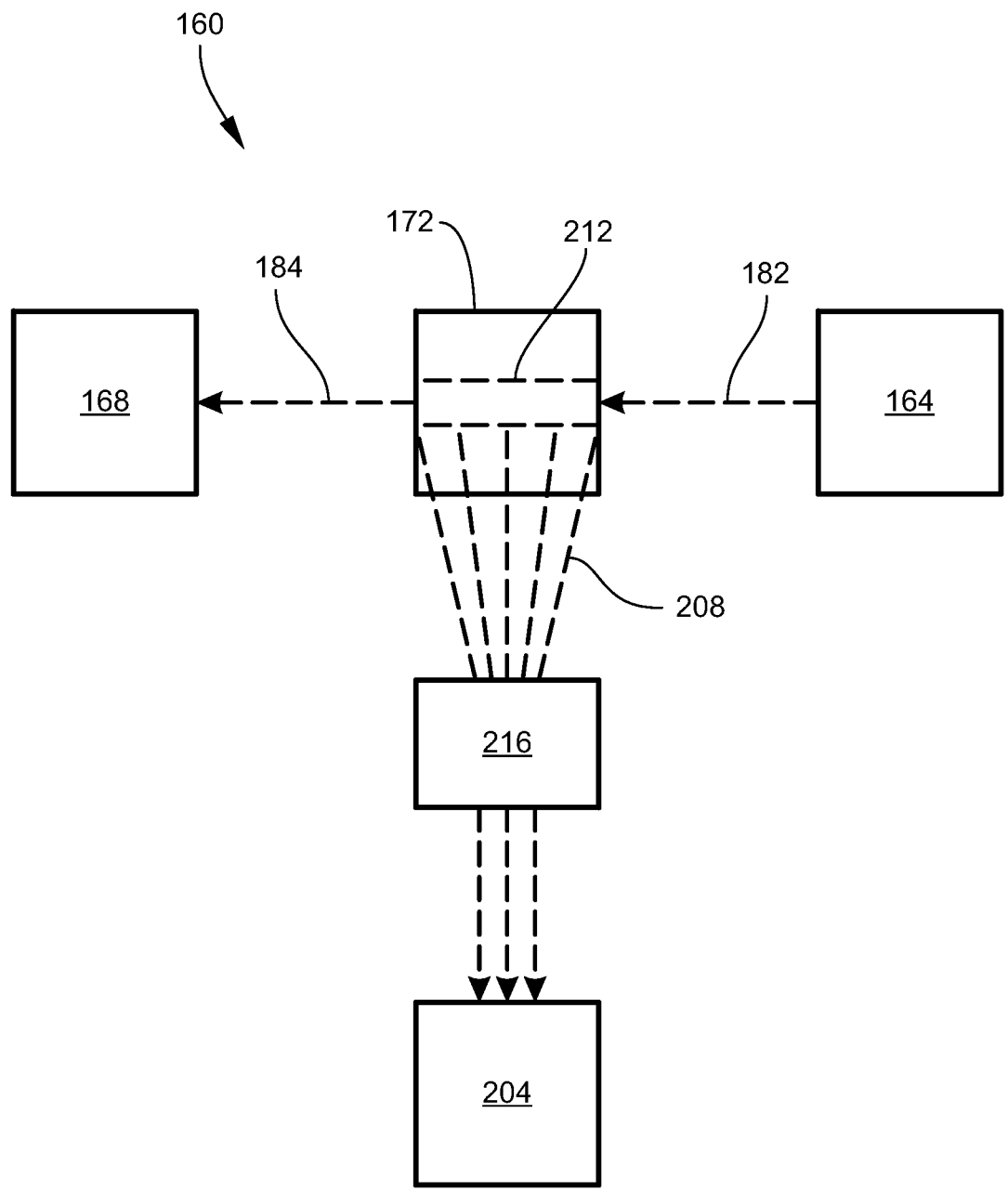

In the implementation described thus far, the aerosol exposure monitor 100 may be characterized as being or including an aerosol collection device (or aerosol sizing and collection device, or particle collection device) 150. The aerosol collection device 150 may include the sample inlet 104, impactor 108, collection filter 112, and pump 116 as described above. In another implementation, the aerosol exposure monitor 100 may also include a nephelometer 160 that is integrated with the aerosol collection device 150 to measure concentrations of the aerosol sized by the impactor 108. The nephelometer 160 is schematically illustrated in FIGS. 1 and 2. The nephelometer 160 includes a light source 164, a light trap 168, and a light detector 204. To facilitate integration of the nephelometer 160 with the aerosol collection device 150 and to provide a sample volume for the nephelometer 160, in the illustrated example the aerosol exposure monitor 100 includes a sample chamber 172 interposed between the impactor 108 and the collection filter 112. Accordingly, the aerosol exiting the impactor 108 (or the last impactor stage) flows through the sample chamber 172 and to the collection filter 112 along a first axis generally depicted by arrows 174, 176 in FIG. 1. Insofar as the sample chamber 172 is part of the fluid flow path through the aerosol collection device 100 and also part of the optical path through the nephelometer 160, the sample chamber 172 may be characterized as being a component of either or both of the aerosol collection device 150 and the nephelometer 160.

The light source 164 may be any device for generating a beam of irradiating light 182 that propagates at a wavelength (or peak wavelength) for suitable for nephelometry. As examples, the light source 164 may be a light emitting diode (LED) or a laser diode (LD). In some implementations, the light source 164 emits irradiating light 182 at a wavelength ranging from 300 to 800 nm. In one specific implementation, the light source 164 emits irradiating light 182 at a wavelength of 785 nm. In operation, the beam of irradiating light 182 propagates into the sample chamber 172 along a second axis that is at an angle to the first axis along which the aerosol flows. In some implementations, the second axis is orthogonal to the first axis. The light trap 168 is located along the second axis on the side of the sample chamber 172 opposite to the light source 164 (i.e., on-axis with the light source 164). Accordingly, any portion 184 of the irradiating light propagating through the sample chamber 172 without being scattered by the aerosol will enter the light trap 168. The light trap 168 may, for example, be a chamber defined by opaque or anti-reflective surfaces, and/or may include geometries or structures configured for trapping light as appreciated by persons skilled in the art. Hence, the unscattered portion 184 of the irradiating light passing through the sample chamber 172 is absorbed by the light trap 168 and is not reflected back into the sample chamber 172, thereby minimizing the possibility that the unscattered light 184 interferes with the measurement of the scattered light and hence improving the sensitivity and detection limits of the nephelometer 160. Apertures (not shown) along the optical path may also be sized and positioned to minimize interference with the desired measurement. To minimize noise in the detection signal, the light source 164 may be pulsed so that the zero-signal level of the light detector 204 may be measured and accounted for frequently. Optionally, the nephelometer 160 may include an additional light detector (not shown) positioned to monitor the intensity of the irradiating light 182 from the light source 164 or the unscattered light 184 from the sample chamber 172, and thus assess the performance of the light source 164.

FIG. 2 is a schematic view of the nephelometer 160 from the perspective of the top of the sample chamber 172, i.e., with the first axis along which fluid flows directed into the drawing sheet. Light 208 scattered by the aerosol in the sample chamber 172 is transmitted to the light detector 204 at an angle (e.g., ninety degrees) relative to the beam of irradiating light 182, i.e., along a third axis that is at an angle to the second axis as well as the first axis. Due to the compactness of the nephelometer 160, reflective surfaces or components on the side of the sample chamber 172 opposite to the light detector 204 are not needed in typical implementations, but may be included if desired. In some implementations, to increase sensitivity the irradiating light 182 is collimated, but not necessarily focused, and extends across the entire sample chamber flow path. As a result, the irradiating light 182 creates an expanded, generally cylindrical particle sensing volume 212 within the sample chamber 172, as opposed to a line or point generated by a conventionally focused laser beam. In a typical implementation, the cross-section of the generally cylindrical particle sensing volume 212 is oval- or elliptical-shaped, i.e., particle sensing volume 212 is shaped as an elliptic cylinder. This configuration in turn produces a wide, two-dimensional (rectilinear- or rectangular shaped) source of scattered light 208 in the sample chamber 172 for capturing by the light detector 204. The expanded beam may also lower the limit of detection (LOD) of the nephelometer 160, and render the nephelometer 160 less sensitive to vibration. In some implementations, the generally cylindrical sensing volume 212 has a length ranging from 8.0 to 12.0 mm and a diameter (or major axis in the case of an elliptical cross-section) ranging from 0.5 to 2.0 mm. As illustrated in FIG. 2, the scattered light 208 may be collected by optics 216 (e.g., one or more lenses of appropriate design) before being transmitted to the light detector 204.

The light detector 204 may be any detector suitable for collecting light in nephelometry applications. As examples, the light detector 204 may be a photodiode, an avalanche photodiode, or other type of compact light detector. The light detector 204 may be configured to take advantage of the rectangular-shaped beam of scattered light 208 emitted from the sample chamber 172 by having as wide a sensing area as possible in the available space. Accordingly, in some implementations, the light detector 204 includes a rectilinear-shaped (e.g., rectangular-shaped) active sensing area. This configuration enables a more complete capture of the scattered light 208 while minimizing the space needed for the optics. In one example, the size of the sensing area is 2 mm by 3 mm. One non-limiting example of a suitable light detector 204 is a blue/green enhanced photodiode-preamplifier available as model no. ODA-6WB-500M from Opto Diode Corp., Newbury Park, Calif.

In operation, the nephelometer 160 may be operated simultaneously with the aerosol collection device 150, whereby nephelometric data (e.g., total scattering potential) is collected in real time and in situ while particles are being sized and collected by the collection filter 112. The combination of the nephelometer 160 and the aerosol collection device 150 enables both acute and chronic exposure data to be collected simultaneously. That is, the nephelometer 160 measures acute responses (e.g., minimum or peak levels of exposure) in real time while the aerosol collection device 150 enables the acquisition of chronic (long-term) data that may be integrated or averaged over the total sampling period (e.g., day, week, etc.). By enabling the collection of total aerosol over time as an integral part of the optical bench of the nephelometer 160, the aerosol exposure monitor 100 is able to collect acute and chronic exposure data without losing any of the aerosol being sampled, i.e., there are no internal sample losses. This approach provides a gravimetrically-based calibration against which to normalize the concurrent mathematical integration of the simultaneous real-time data file. Data from the light detector 204 may be logged in a memory of the aerosol exposure device 100 and later downloaded to a computing device for analysis. In some implementations, the nephelometer 160 has a dynamic range of 2 to 10,000 $\mu g/m^3$ and a resolution of 1 $\mu g/m^3$, i.e., is able to detect a 1 $\mu g/m^3$ change in concentration.

It will also be noted that gravimetric data acquired from the collection filter 112 may be utilized as an accurate referee calibration for the nephelometer 160. That is, the integrated real-time data concentration by definition should equal the gravimetric filter calibration.

Figure 3:
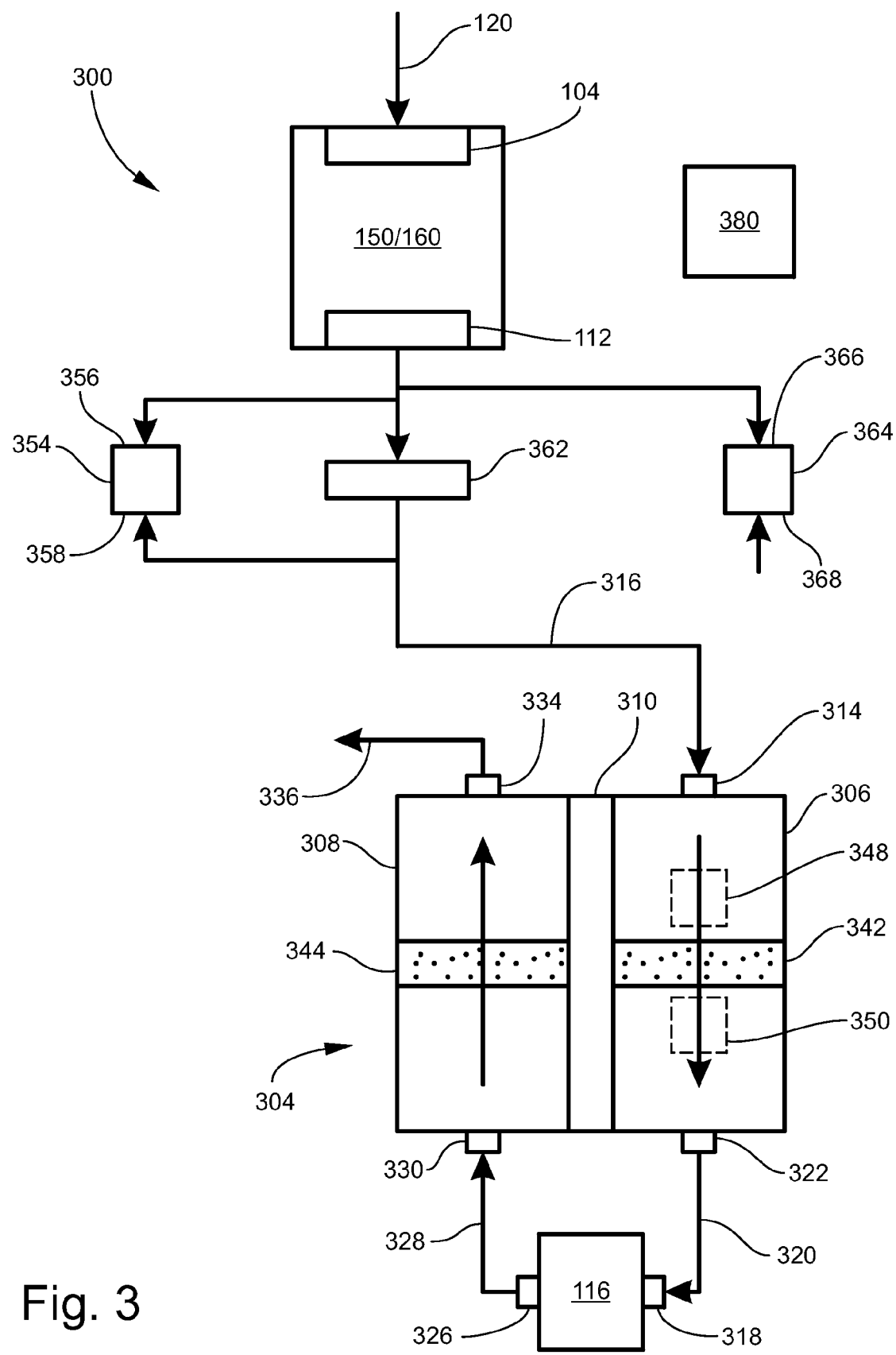

FIG. 3 is a schematic view of an example of an aerosol exposure monitor (or monitoring apparatus, or monitoring device) 300 according to another implementation of the present disclosure. The aerosol exposure monitor 300 generally includes an aerosol collection device, a pump (such as, for example, the pump 116 described above and illustrated in FIG. 1), and a noise dampening device (or gas flow pulsation and noise dampening device) 304. In some implementations, the aerosol collection device includes a sample inlet and a collection filter (e.g., the sample inlet 104 and collection filter 112 described above and illustrated in FIG. 1). In some implementations, the aerosol collection device may correspond to the aerosol collection device 150 described above and illustrated in FIG. 1. The aerosol exposure monitor 300 may also include a nephelometer, which may correspond to the nephelometer 160 described above and illustrated in FIGS. 1 and 2 and which thus may be integrated with the aerosol collection device in the manner described above and illustrated in FIGS. 1 and 2.

The noise dampening device 304 may include an inlet chamber 306, an outlet chamber 308, and an elastomeric (or deformable) membrane 310 interposed between and fluidly isolating the inlet chamber 306 and the outlet chamber 308. The inlet chamber 306 is in fluid communication with the aerosol collection device 150, such as the outlet side of the collection filter 112 in. For this purpose the inlet chamber 306 may include a first port 314, which may, for example, be configured as a connector that is coupled to a suitable fluid conduit 316 (e.g., a tube). The inlet chamber 306 is also in fluid communication with an inlet 318 of the pump 116, which may be accomplished via conduit 320 connected to a second port 322 of the inlet chamber 306. The outlet chamber 308 is in fluid communication with an outlet 326 of the pump 116, which may be accomplished via a conduit 328 connected to a third port 330 of the outlet chamber 308. The outlet chamber 308 is also in fluid communication with a fourth port (exhaust port) 334. The fourth port 334 may be open to an interior of the aerosol exposure monitor 300, or may be connected to a conduit (exhaust tube 336) and filtered if there is concern that emissions from the pump may cross-contaminate the nephelometer or filter collection systems. This exhaust tube 336 may be open to the interior of the aerosol exposure monitor 300 or may communicate with an opening leading to the outside of the aerosol exposure monitor 300. The noise dampening device 304 thus establishes (or defines) an inlet flow path through the inlet chamber 306 directed into the pump 116, and an outlet (or exhaust) flow path through the outlet chamber 308 directed out from the pump 116.

The elastomeric membrane 310 serves as the boundary between the inlet chamber 306 and the outlet chamber 308, and hence is exposed to the fluid flowing through inlet chamber 306 and the fluid flowing through the outlet chamber 308. For this purpose, the elastomeric membrane 310 may be configured as a planar structure or sheet. The elastomeric membrane 310 may have any suitable shape, such as a rectilinear or other polygonal shape, or a circular or other rounded shape. The shape of the elastomeric membrane 310 may be the same as or similar to that of the inlet chamber 306 and the outlet chamber 308. The size of the elastomeric membrane 310 may depend on the size of the inlet chamber 306 and the outlet chamber 308, in that the elastomeric membrane 310 should be large enough to serve as a complete boundary between the inlet chamber 306 and the outlet chamber 308. In one example, the elastomeric membrane 310 is a square having one-inch sides and a thickness of 0.010 inch. In other examples, the area of the elastomeric membrane 310 may range from 5.0 to 15.0 cm, and the thickness may range from 0.125 to 0.5 mm.

The elastomeric membrane 310 is exposed to the pressure pulsations and acoustical vibrations generated by the flow of gas in both the inlet chamber 306 and the outlet chamber 308. The elastomeric membrane 310 has been found to be highly effective in dampening these pulsations and vibrations and minimizing the system burden caused by the pump noise level. Without wishing to be bound by any particular theory at the present time, it is believed that dampening effectiveness may be attributed to the flexibility of the elastomeric membrane 310, and its interposition between the respective gas flows in the inlet chamber 306 and the outlet chamber 308 whereby pressure and acoustical waves propagating to one side of the elastomeric membrane 310 may partially or wholly cancel out pressure and acoustical waves propagating to the opposing side of the elastomeric membrane 310. In one non-limiting example, a composition of the elastomeric membrane 310 found to exhibit effective dampening is silicone rubber. It will be understood, however, that other compositions may also be suitable for functioning as the elastomeric membrane 310 in the presently disclosed noise dampening device 304.

As also illustrated in FIG. 3, the noise dampening device 304 may include a fluid filter 342 spanning the cross-sectional flow area of the inlet chamber 306 to prevent any particles in the gas stream from entering the pump 116. Alternatively or additionally, the noise dampening device 304 may include another fluid filter 344 spanning the cross-sectional flow area of the outlet chamber 308 to prevent any particles in the gas stream discharged from the pump 116 from contaminating the interior of the aerosol exposure monitor 300. The fluid filter 342, 344 should have a composition that does not unduly restrict gas flow. In one example, the fluid filter 342, 344 is an open cell polymeric foam such as an open cell polyurethane foam (PUF). In one example, the cross-sectional area of the fluid filter 342, 344 encountered by the flowing gas is 1.4 inches in length and 0.25 inch in height. Without wishing to be bound by any particular theory at the present time, it is proposed that the provision of one or more fluid filters 342, 344 as described and illustrated herein may serve a role in the noise attenuation achieved by the noise dampening device 304.

As further illustrated in FIG. 3, the noise dampening device 304 may be utilized as a housing or enclosure for containing one or more sensors configured to measure one or more properties of the gas flowing through the aerosol exposure monitor 300. Typically, such properties are more accurately measured upstream of the pump 116, and thus the sensors may be located so as to be exposed to the gas flowing through the inlet chamber 306. In the illustrated example, a temperature sensor 348 and a relative humidity (RH) sensor 350 are located in or at the inlet chamber 306. The temperature sensor 348 and RH sensor 350 may be placed in signal communication with the electronics of the aerosol exposure monitor 300 by any suitable means. For example, the temperature sensor 348 and RH sensor 350 may be provided in the form of chips or other structures that are mounted to a printed circuit board (PCB) of the aerosol exposure monitor 300. In this case, the temperature sensor 348 and RH sensor 350 may protrude through cut-outs formed in the side of the noise dampening device 304 facing the PCB. Appropriate seals may be provided at the interfaces between the temperature sensor 348 and RH sensor 350 and their respective cut-outs to prevent fluid loss from the noise dampening device 304. In alternative implementations, the temperature sensor 348 and RH sensor 350 may be positioned in-line with the fluid flow path at locations outside of the noise dampening device 304.

Data from the temperature sensor 348 and RF sensor 350 may be logged in a memory of the aerosol exposure monitor 300 and utilized—either during operation or subsequently after downloading the data to a computing device—to correct the nephelometry data generated by the light detector 204, i.e., to compensate for temperature and RH. This data may also be utilized in real time by the processing electronics of the aerosol exposure monitor 300 to control or adjust the pump 116 and thereby control or adjust the flow rate through the aerosol exposure monitor 300. This data may also be utilized as quality control (QC) data to indicate the operating conditions that transpired during the sampling period.

As also illustrated in FIG. 3, the aerosol exposure monitor 300 may include one or more pressure sensors. In the specific example, a first differential pressure sensor 354 is utilized to monitor the flow rate of gas through the aerosol exposure monitor 300 during operation of the pump 116. For this purpose, respective ports 356, 358 of the first differential pressure sensor 354 may be placed in fluid communication with the inlet and outlet sides of an orifice 362 located downstream of the collection filter 112. The differential pressure data produced by gas flow through this orifice 362 may be utilized in real time as a means for controlling the flow rate during operation of the pump 116, and this differential pressure data may also be logged in memory for later downloading as QC data to a computing device to indicate the operating conditions that transpired during the sampling period. Also, a second differential pressure sensor 364 is utilized to monitor the condition of the sample inlet 104 and the collection filter 112, i.e., to determine whether the sample inlet 104 was blocked or obstructed during operation and the rate of aerosol buildup on the collection filter 112 and thus identify short periods of significantly high loading. For this purpose, one port 366 of the second differential pressure sensor 364 may be placed in fluid communication with the fluid flow path at a point downstream of the collection filter 112, while another port 368 is open to the interior of the aerosol exposure monitor 300 to measure ambient pressure. The pressure data from the second differential pressure sensor 364 may be utilized in real time to indicate an alarm condition and/or to automatically terminate the sampling process if the pressure drop is too large to maintain adequate flow rate control. The pressure data from the second differential pressure sensor 364 may also be logged in memory for later downloading as QC data to a computing device to indicate the operating conditions that transpired during the sampling period.

As also illustrated in FIG. 3, the aerosol exposure monitor 300 may include one or more accelerometers for monitoring motion of the aerosol exposure monitor 300 along one or more directions (axes). In the illustrated example, a single tri-axial accelerometer 380 configured for measuring acceleration in three directions is provided. The accelerometer 380 may be provided in the form of a microfabricated or MEMS-based chip that is mounted to the PCB of the aerosol exposure monitor 300. One example of a suitable accelerometer 380 is an Okidata 8953 accelerometer. The data produced by the accelerometer 380 may be logged in memory for later downloading as QC data to a computing device. In implementations where the aerosol exposure monitor 300 is utilized as a personal level exposure monitoring device, the accelerometer data may be utilized to provide an indication of wearing (protocol) compliance, i.e., to verify that the user was wearing the aerosol exposure monitor 300 during the time periods called for during the sampling period. The accelerometer data may also be utilized to determine the activities in which the user was engaged during the sampling period (e.g., personal energy expenditure associated with sitting, walking, exercising, etc.), and this data may be correlated with the exposure data recorded by the light detector 204 over the same sampling period. In implementations where the aerosol exposure monitor 300 is utilized as a stationary device in an indoor or outdoor setting, the accelerometer 380 may be utilized as a QC or security measure to determine whether the aerosol exposure monitor 300 was moved accidentally or without authorization.

In other implementations, FIG. 3 more generally represents a gas processing device (300) of any type whose operation entails active gas flow through the gas processing device and which may benefit from the pulse and/or noise dampening functionality of the noise dampening device 304. The gas processing device generally includes a housing (not shown), a sample inlet providing flow communication into the housing, and a pump and the noise dampening device 304 disposed in the housing. The gas processing device may include fluid circuitry (or plumbing) and one or more types of instruments, detectors, sensors and the like communicating with the gas flow path through the housing. In addition to an aerosol exposure monitor, aerosol collection device, nephelometer such as described by example above, other examples of the gas processing device may be (or be part of) any other type of instrument that acquires data from aerosols, or a gaseous sample introduction device that supplies the sample to a downstream instrument or reaction vessel, or a spectrometric instrument (e.g., gas chromatograph), a spectroscopic instrument (e.g., a Raman spectroscopic instrument), etc.

Figure 4:
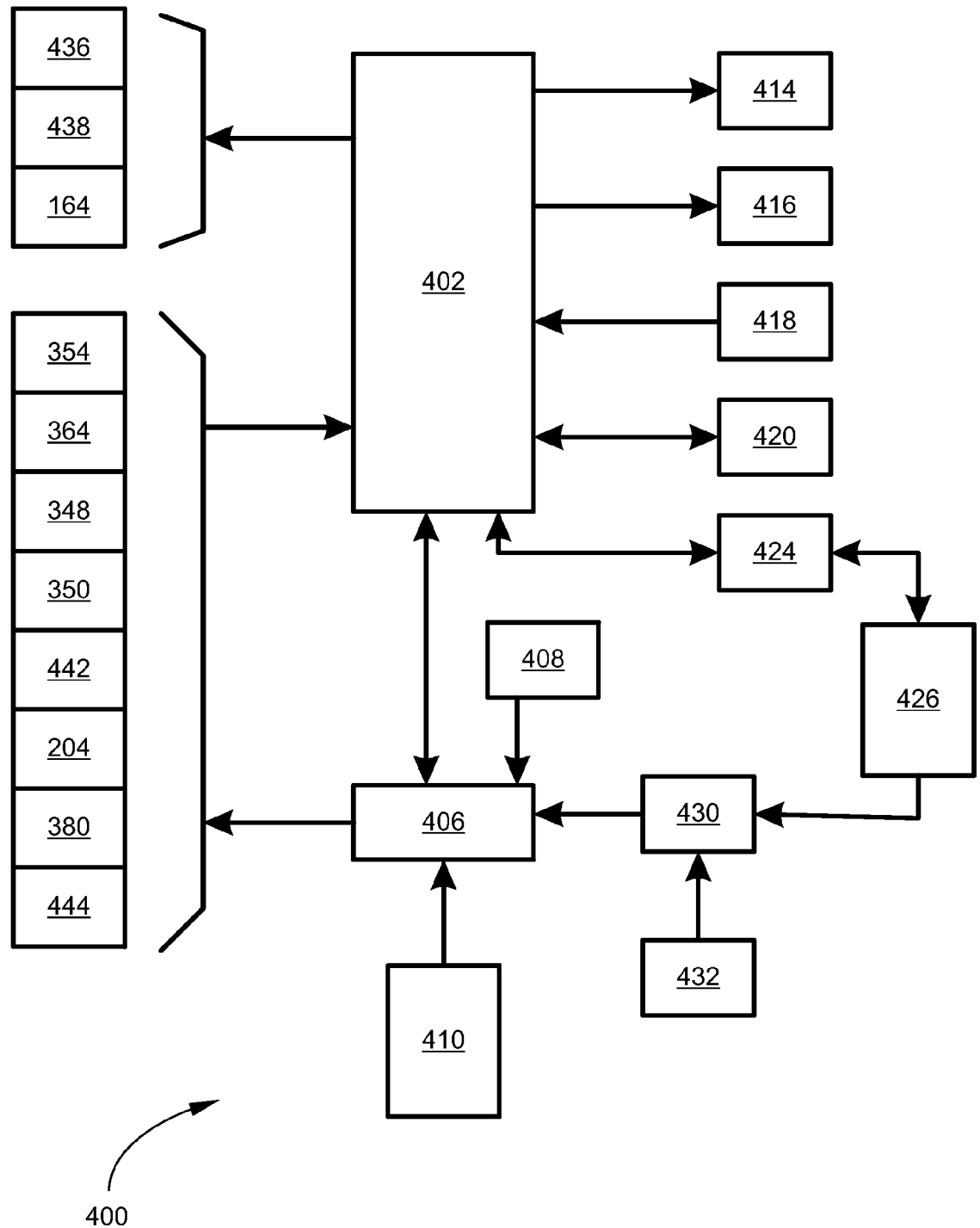

FIG. 4 is a schematic (or functional block) diagram 400 illustrating various signal processing functions that may be implemented by the aerosol exposure monitor 300 (or 100). Persons skilled in the art will appreciate that various functions (modules, circuitry, etc.) illustrated in FIG. 4 may be implemented by hardware (or firmware), software, or both. Moreover, it will be appreciated that many of the functions illustrated in FIG. 4 may be implemented by circuitry provided on a PCB contained in the housing of the aerosol exposure monitor 300. In FIG. 4, an electronic controller 402 is representative of one or more microcontrollers, microprocessors, application specific integrated circuits (ASICs), digital signal processors (DSPs), or the like; a real time clock; sensor input/output (I/O) interfaces; analog-to-digital converters (ADCs), digital-to-analog converters (DACs); programmable memory; data logging memory; and selectable parameter settings. In some implementations, the electronic controller 402 includes a 16 MB onboard memory and an 8 MHz processor.

The electronic controller 402 may communicate with a power management module 406, which may also communicate with a real time clock battery 408 and a system battery pack 410. The electronic controller 402 may also communicate with one or more user interfaces such as, for example, LED indicators 414, a small display screen 416 such as a liquid crystal display (LCD) screen, and pushbuttons 418. The electronic controller 402 may also optionally communicate with a wireless transceiver 420. The electronic controller 402 may also communicate with a data communication interface 424 such as a universal serial bus (USB) interface, which may be connected to a computing device 426 for downloading and uploading of data. For example, software executed by the computing device 426 may be utilized to process and display data received from the aerosol exposure monitor 300 (or 100) subsequent to a sampling operation, and/or to set operating parameters prior to a sampling operation. Optionally, the computing device 426 may also communicate with a power converter 430 (e.g., USB interface) to provide power to the power management module 406. As another option, an AC power adapter 432 may communicate with the power converter 430 to provide line power from an external power source. The electronic controller 402 may also communicate with one or more outputs such as, for example, audio and/or visual alarms 436, a pump drive 438 for controlling the pump 116, and the light source 164 for controlling ON/OFF cycling. The electronic controller 402 may also communicate with one or more inputs to receive data therefrom, and the power management module 406 may communicate with one or more inputs to provide power if necessary for their operation. Examples of such inputs may include, but are not limited to, the first differential pressure sensor 354, the second differential pressure sensor 364, the temperature sensor 348, the RH sensor 350, battery voltage check 442, the light detector 204, the accelerometer 380, and an optional GPS receiver 444. It can be seen that various types of QC data may be collected and stored by the electronic controller 402 and made available for download to the computing device 426, thereby enabling robust post-collection validation.

The aerosol exposure monitor 300 (or 100) may be configured for use as an indoor monitor, an outdoor monitor, an in-vehicle monitor, or a personal monitor. As an indoor or outdoor monitor, the aerosol exposure monitor 300 may be placed in any fixed location where it is desired to sample aerosol in the immediate vicinity. As noted above, the aerosol exposure monitor 300 may be connected to a wall outlet or any other source of external power. As an outdoor monitor, the aerosol exposure monitor 300 may be placed in a suitable package, or its housing may be modified, as necessary to withstand outdoor conditions. As a personal monitor, the aerosol exposure monitor 300 may be configured so as to be easily wearable by the user in an unobtrusive manner to ensure compliance by the user in wearing the aerosol exposure monitor 300 during the prescribed periods of operation. For instance, the aerosol exposure monitor 300 may be sized so as to be comfortably worn in a pocket of the user, or in a small holder or bag comfortably worn by the user. In one specific example, the maximum dimensions of the aerosol exposure monitor 300 are 2.7 inches in length, 1.6 inches in depth, and 5.0 inches in height. When utilized as a personal monitor, the aerosol exposure monitor 300 will typically utilize a small number of batteries as noted above. The burden to the user of wearing the aerosol exposure monitor 300 may also be lessened by minimizing its weight. In some examples, the aerosol exposure monitor 300 weighs less than 300 grams. In other examples, the aerosol exposure monitor 300 weighs less than 240 grams. In other examples, the aerosol exposure monitor 300 weighs less than 220 grams. Reduced weight may be accomplished, for example, by employing a lightweight yet robust material such as injection-molded plastic for the housing and as many of the other structural components as possible. The various components housed in the aerosol exposure monitor 300 may be arranged so as to balance its weight, thereby improving the comfort of wearing the aerosol exposure monitor 300 and promoting wearing compliance by the user.

Figure 5:
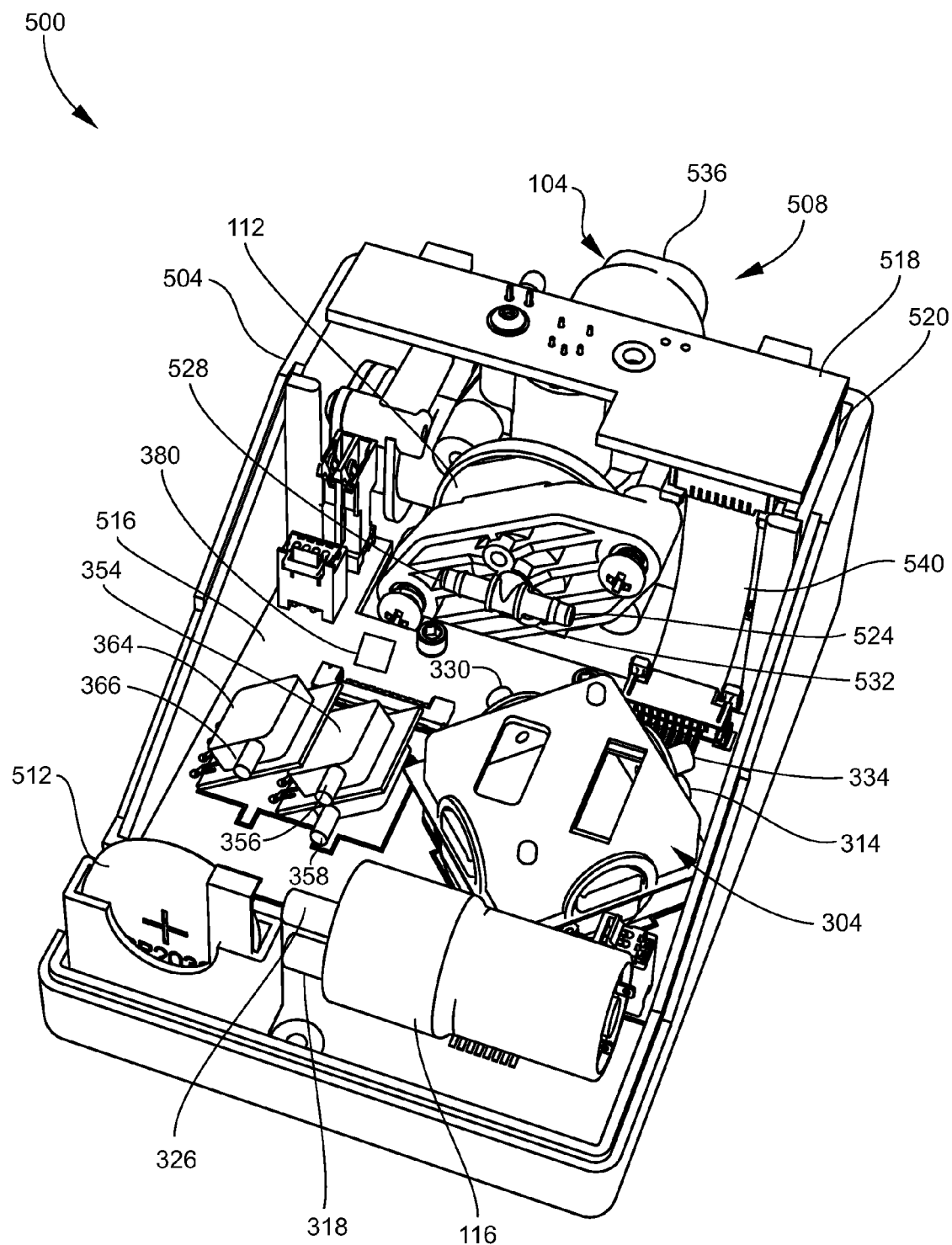
Figure 6:
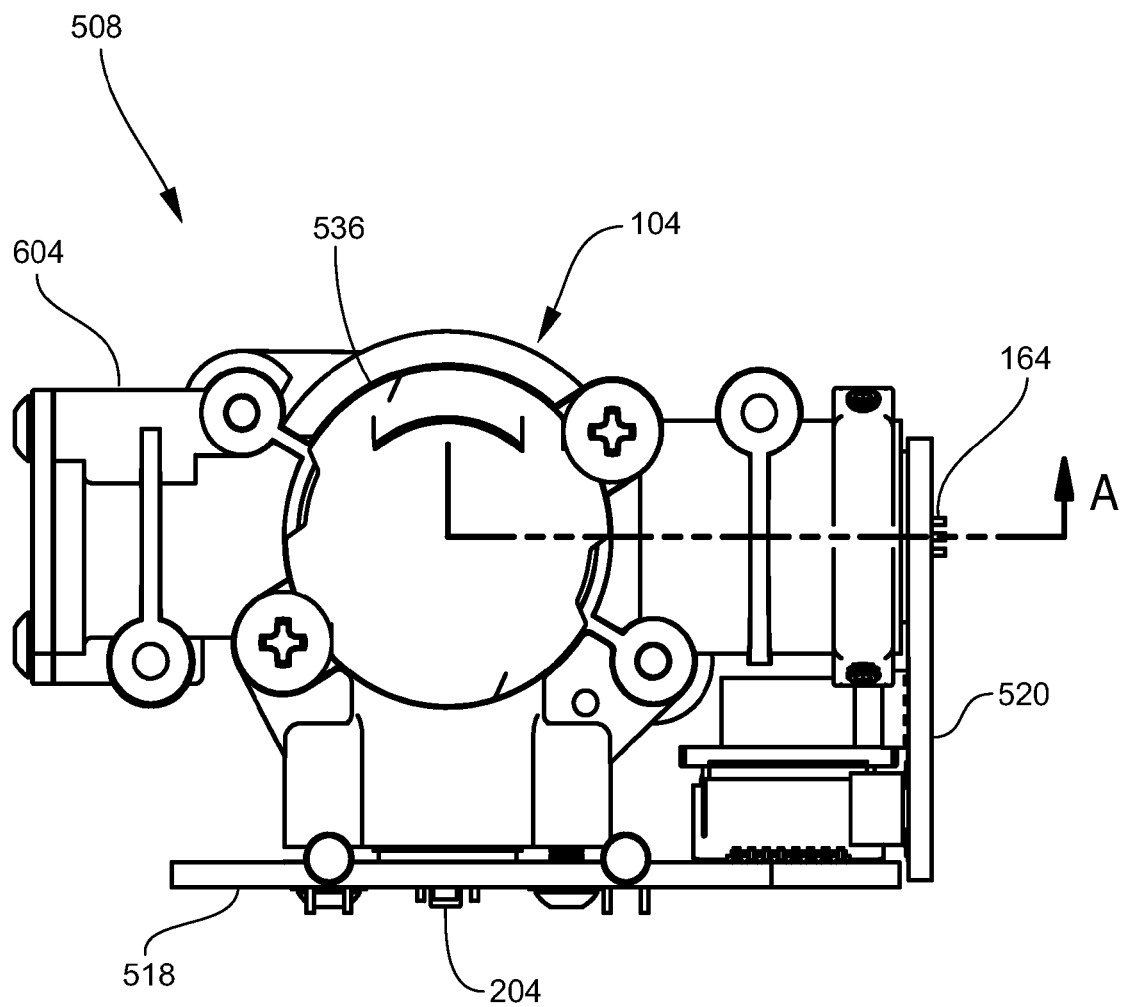
Figure 7:
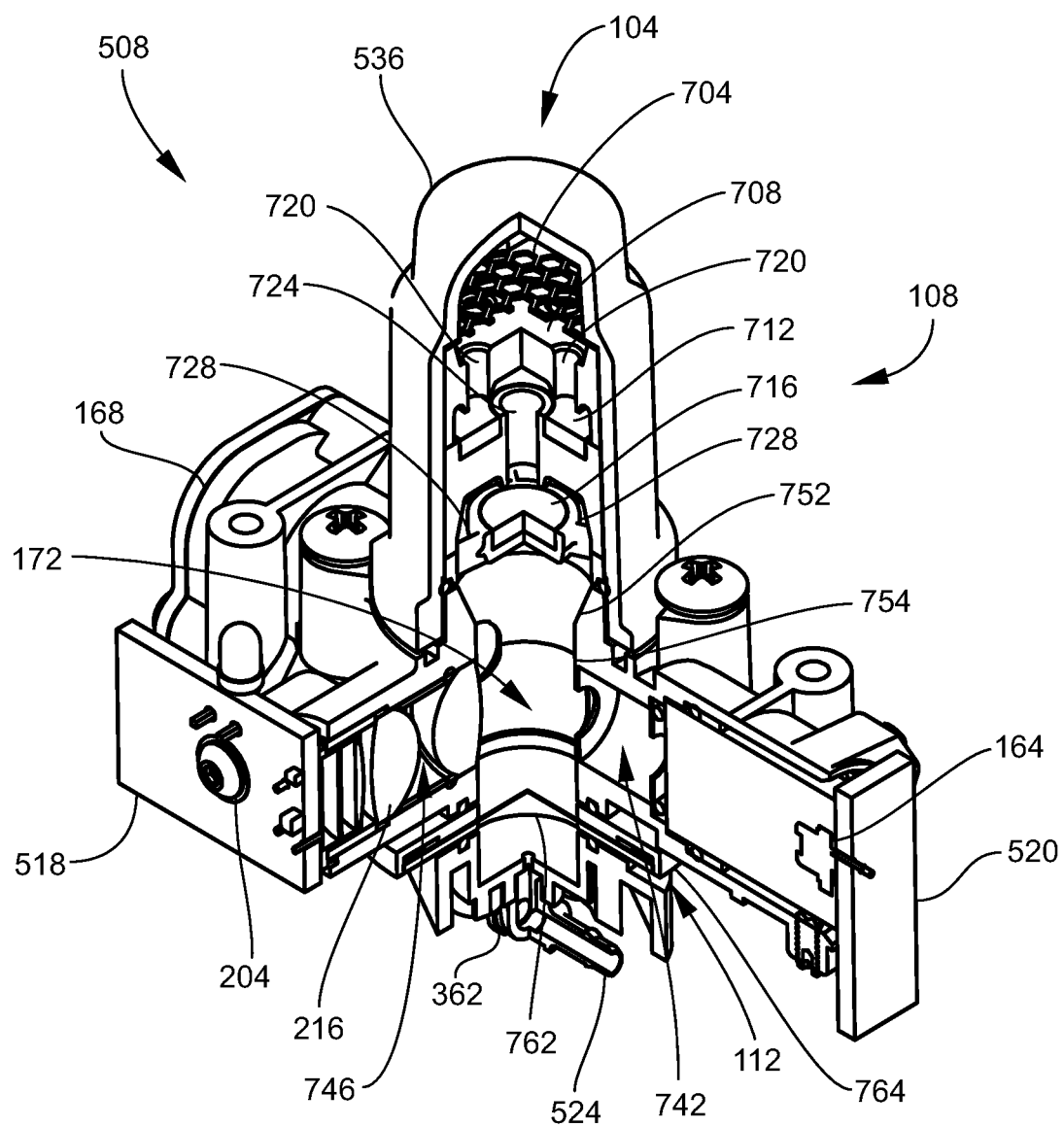
Figure 8:
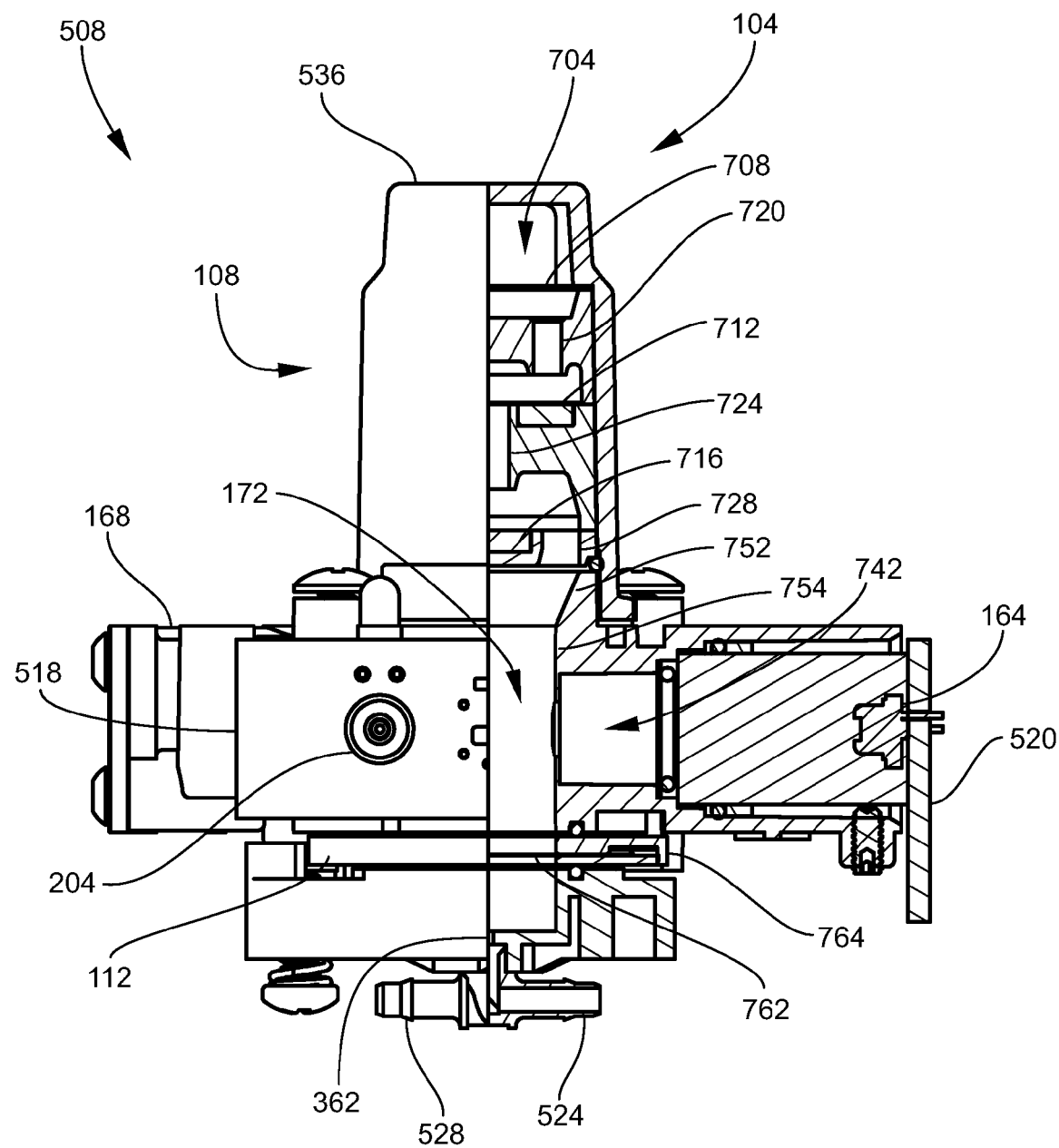
Figure 9:
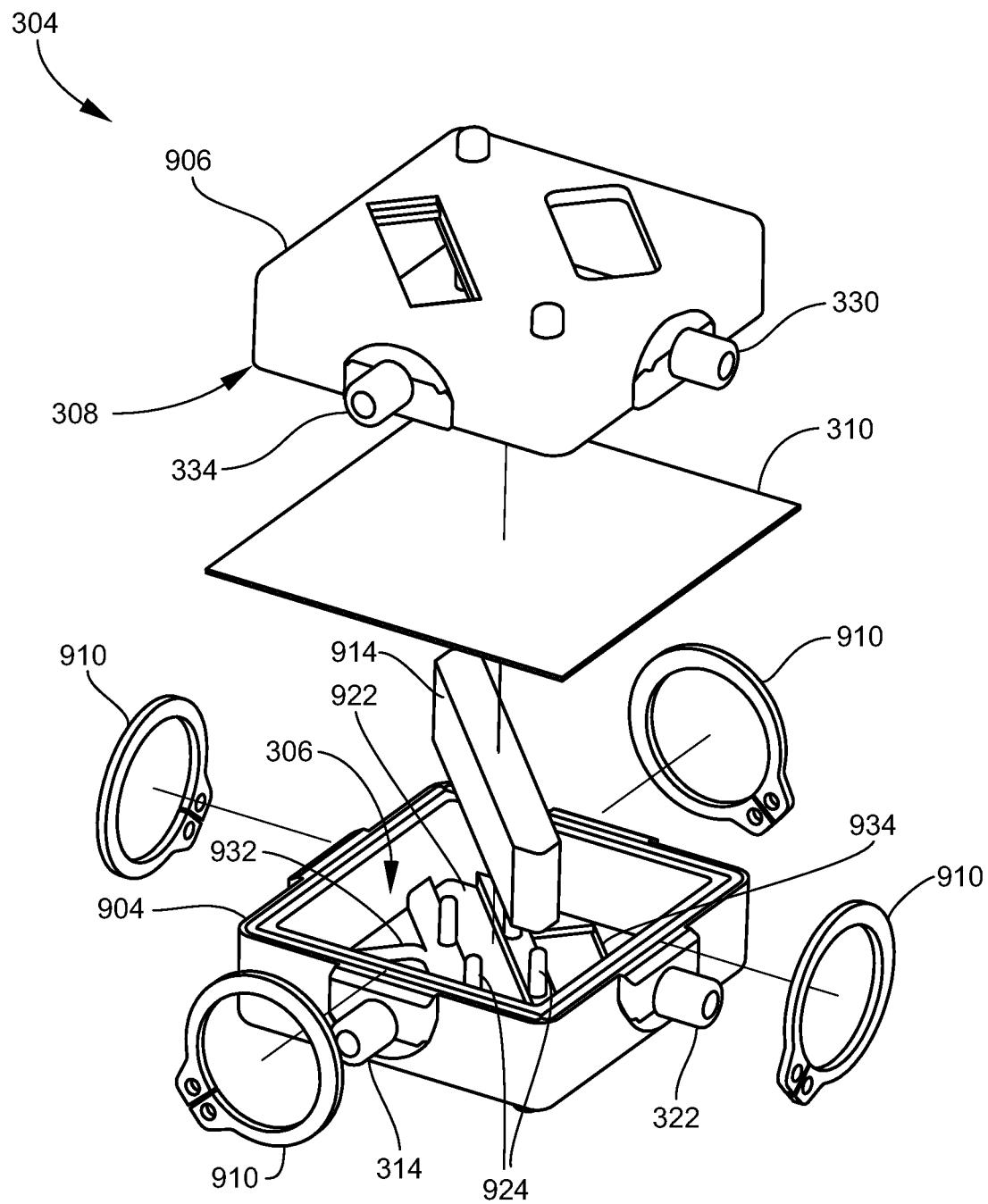
Figure 10:
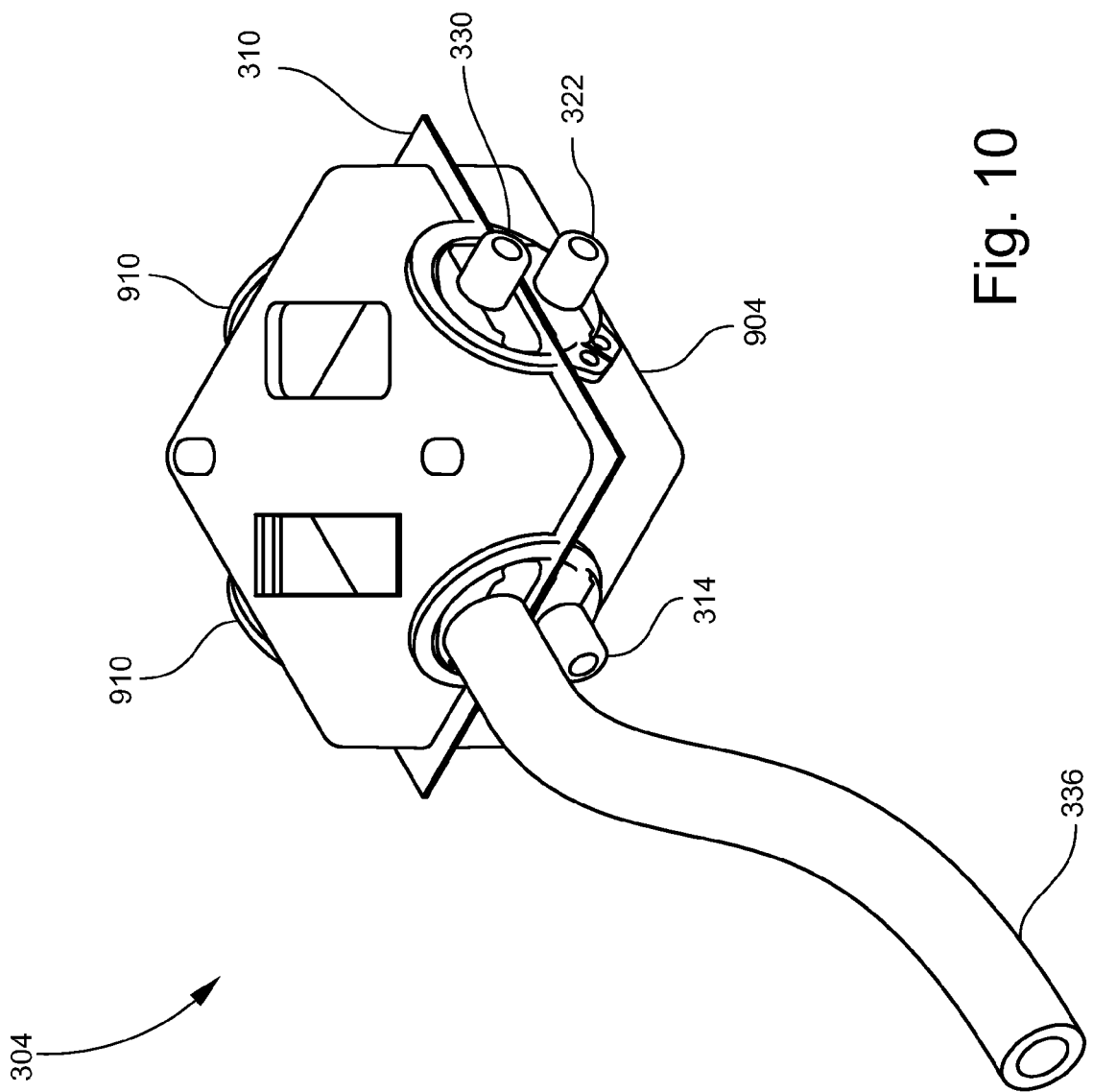
Figure 11:
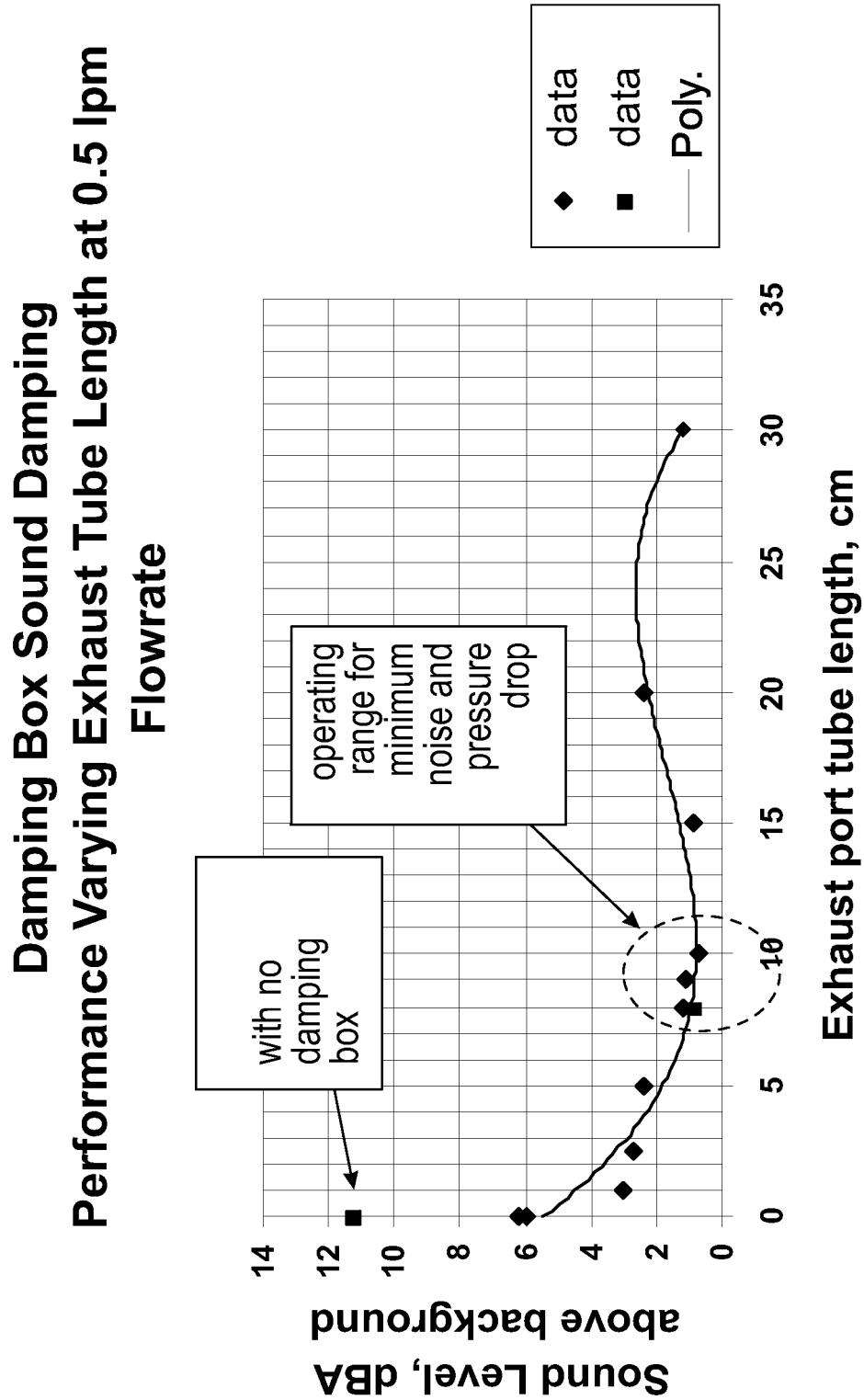

FIGS. 5-10 illustrate an example of an aerosol exposure monitor 500 according to another implementation. The aerosol exposure monitor 500 may include many of the same or similar features as those described above and illustrated in FIGS. 1-4, and accordingly like reference numerals designate like features in FIGS. 5-10. Specifically, FIG. 5 is a perspective view of the aerosol exposure monitor 500 with a portion of its housing 504 removed. FIG. 6 is a top view of an aerosol sampling assembly 508 that includes the aerosol collection device and the nephelometer. FIG. 7 is a perspective view of the sampling assembly 508 with a portion cut-away along line A-A of FIG. 6. FIG. 8 is an elevation view of the sampling assembly 508 with the same portion cut-away as in FIG. 7. FIG. 9 is an exploded view of the noise dampening device 304. FIG. 10 is a perspective view of the noise dampening device 304.

Referring to FIG. 5, the housing 504 may be configured to be opened in the manner shown to enable removal of the collection filter 112, replacement of the batteries or other components, cleaning of the interior, etc. The housing 504 may provide security features (not shown) to prevent its opening by the user or unauthorized personnel. The removed section (not shown) of the housing 504 may be configured for mounting a set of batteries. A coin-type battery 512 shown in FIG. 5 may be included to provide backup power. As previously noted, the aerosol exposure monitor 500 may be configured for continuous or ON/OFF cycling operation. In one example in which three AA batteries are employed, the aerosol exposure monitor 500 is capable of operating for 40 hours in continuous mode and 168 hours in ON/OFF cycling mode. The exposure monitor 500 may include various user interfaces as needed or desired, such as control buttons, a keypad, a display, LED indicators, a high-level alarm, etc.

The aerosol exposure monitor 500 may include a main PCB 516 that provides all or most of the electronics, and may also include one or more additional PCBs 518, 520 as needed. In FIG. 5, the accelerometer 380 has been arbitrarily located. FIG. 5 also shows the assembly of the aerosol collection device and the nephelometer, including the sample inlet 104 which is located external to the housing 504. A port 524 communicating with the flow orifice 362 (FIG. 7) below the removable collection filter 112 is connected via a tube (not shown) to the first port 314 of the inlet chamber 306 (FIG. 9) of the noise dampening device 304. The second port 322 (FIG. 9) of the inlet chamber 306 is connected via a tube (not shown) to the inlet port 318 of the pump 116. The outlet port 326 of the pump 116 is connected via a tube (not shown) to the third port 330 of the outlet chamber 308 (FIG. 9) of the noise dampening device 304. The fourth port 334 of the outlet chamber 308 is connected to the exhaust tube 336 (FIG. 10) of the noise dampening device 304. In the present example, the exhaust tube 336 opens into the interior of the housing 504. Another port 528 (FIG. 5) communicating with the outlet side of the flow orifice 362 (FIG. 7) is connected via a tube (not shown) to a port 358 of the first differential pressure sensor 354. At a point just below the removable collection filter 112, another port 532 (FIG. 5) communicating with the inlet side of the flow orifice 362 is connected via a tube (not shown) to another port 356 of the first differential pressure sensor 354. This port 532 is also connected to a port 366 of the second differential pressure sensor 364. Another port (not shown) of the second differential pressure sensor 364 is open to communicate with the interior of the housing 504.

In some implementations, the tubing utilized to interconnect the differential pressure sensors 354, 364 to the various ports described above is capillary-sized tubing. In one non-limiting example, the inside diameter of the tubes is 0.010 inch or thereabouts. A very minute bidirectional fluid flow occurs in the tubes as pressure changes, and as the pressures in the respective ports of the differential pressure sensors 354, 364 changes. Due to the restrictive, small inside diameters of the tubes, these pressure changes are pneumatically damped by the tubes and by the internal volume of the corresponding ports of the differential pressure sensors 354, 364. By this configuration, the small-diameter tubes act as resistors and the corresponding ports of the of the differential pressure sensors 354, 364 act as capacitors, greatly smoothing the pressure spikes and thereby smoothing the electronic signal produced by the differential pressure sensors 354, 364. It has been found that this pneumatic damping of the pressure in the tubes is more effective for obtaining a smooth average sensor reading than electronic damping of the signal by means of conventional resistive/capacitive filter networks.

Referring to FIGS. 6-8, the sampling assembly 508 includes a cap 536 that defines the sample inlet 104 and encloses the impactor 108. The cap 536 defines one or more inlet openings (not shown) oriented to admit aerosol from a side direction. In this example, only one inlet opening is used. The inlet opening may include a screen (not shown). Aerosol flowing into the inlet opening is turned ninety degrees in an inlet plenum 704 defined by the cap 536 and then flows through a coarse inlet screen 708, which scalps particles larger than a selected coarse size as described earlier in this disclosure. In this example, the impactor 108 includes a first impactor stage and a second impactor stage, which respectively include a first impactor plate 712 and a second impactor plate 716. The impactor plates 712, 716 may each have an oil retained within a porous, sintered material or coating their surfaces to minimize particle bounce. In one non-limiting example, the oil is a silicone oil.

In operation, the pump 116 draws ambient aerosol into the opening of the sample inlet 104 and through the impactor 108. The aerosol passing through the coarse inlet screen 708 flows toward one or more passages 720 radially offset from the central axis of the impactor 108. Particles too large to change momentum do not reach the radially offset passages 720 and are consequently removed from the aerosol stream. The remaining aerosol flows through the radially offset passages 720 to the first impactor stage. The aerosol is then forced to change direction (e.g., make a turn) and, in a laminar regime to minimize surface losses, flows across the first impactor plate 712 toward a central passage 724. Particles larger than the cut-point of the first impactor stage are not able to remain entrained in the aerosol stream and instead impact the first impactor plate 712. The remaining aerosol flows through the central passage 724 to the second impactor stage. The aerosol is then forced to change direction yet again and flows across the second impactor plate 716 toward one or more radially offset passages 728. Particles larger than the cut-point of the second impactor stage are not able to remain entrained in the aerosol stream and instead impact the second impactor plate 716. The remaining aerosol then flows through the radially offset passages 728, through the sample chamber 172 and onto the collection filter 112. In one example, the collection filter 112 has an exposed area of filter material facing the sample chamber 172, and the diameter of the exposed area ranges from 6 to 20 mm. The gas (filtered aerosol) is drawn through the flow orifice 362 below the collection filter 112 and flows to the noise dampening device 304 and differential pressure sensors 354, 364 as described above.

The sampling assembly 508 also includes a nephelometer housing 604 that encloses the light source 164, the light trap 168, the light detector 204, optics 216, and various apertures. The sampling assembly 508 includes PCBs 518, 520 on which the light source 164 and light detector 204 are respectively mounted. The circuitry of the PCBs 518, 520 communicates with the main PCB 516 via a ribbon cable 540 (FIG.

5). A portion of the nephelometer housing 604 encloses a first bore 742 that defines the path of irradiating light from the light source 164. Another portion of the nephelometer housing 604 encloses an orthogonal second bore 746 that defines the path of scattered light directed to the light detector 204.

The sample chamber 172 is shaped and sized such that the sample chamber 172 is free or substantially free of turbulent flow—or, stated in another way, the flow of the aerosol is entirely or substantially laminar from the outlet side of the impactor 108, through the sample chamber 172 and to the flow orifice 362. For the range of flow rates contemplated (e.g., 0.5 liters/min) and depending on other operating conditions, this may correspond to the Reynolds number characterizing the aerosol flow being maintained below 1000, or below 250. In the present implementation, to maintain laminar flow the sample chamber 172 is relatively large. In some implementations, the sample chamber 172 has a total length from the impactor 108 to the collection filter 112 ranging from 20 to 22 mm and a cross-sectional dimension ranging from 9 to 14.4 mm. The cross-sectional dimension depends on the shape of the cross-section, for example an inside diameter in the case of a circular cross-section, a major axis in the case of an elliptical cross-section, etc. In one example, the sample chamber 172 has a total length of 20.98 mm and internal diameters ranging from 13.50 mm to 10.00 mm. In the illustrated example, the sample chamber 172 has an upper tapered section 752 and a lower section 754. The lower section 754 may have a constant inside diameter; for example, the lower section 754 may be cylindrical. In one example, the upper tapered section 752 has a length of 4.38 mm, an upper internal diameter of 13.50 mm, a lower internal diameter of 10.00 mm, and a taper between the upper and lower internal diameters. In this example, the lower section 754 has a length of 16.60 mm and an internal diameter of 10.00 mm. Moreover, the sample chamber 172 may generally be free of any edges or corners. Abrupt changes in geometry are avoided to prevent localized turbulence. The laminar flow minimizes the pressure drop through the collection filter 112, minimizes the possibility that the collection filter 112 will become overloaded, minimizes internal aerosol losses, and minimizes the power required from the batteries to run the pump 116 and thereby allows the pump 116 to run for extended periods, e.g., a week or longer. Additionally, the laminar flow and the large sensing volume provided by the sample chamber 172 improves the sensitivity and accuracy of the nephelometric data collected.

As best shown in FIG. 7, the collection filter 112 includes a filter element 762 held in a filter holder (or cartridge) 764. The filter holder 764 is designed to be removable from the assembly to facilitate analysis of the particles captured by the filter element 762.

Referring to FIGS. 9 and 10, the noise dampening device 304 includes a housing comprising two housing portions (or housing halves) 904, 906. The first housing portion 904 includes the first port 314 and the second port 322, and the second housing portion 906 includes the third port 330 and the fourth port 334. In assembled form, the elastomeric membrane 310 is sandwiched between the two housing portions 904, 906 by any suitable means of securement. Four retainer clips 910 secure the assembly in this example. Seals such as gaskets may be provided to seal the interfaces between the elastomeric membrane 310 and the housing portions 904, 906. In assembled form, the first housing portion 904 and the elastomeric membrane 310 cooperatively form the inlet chamber 306, and the second housing portion 906 and the elastomeric membrane 310 cooperatively form the outlet chamber 308. One or both housing portions 904, 906 may include a fluid filter 914, only one of which is visible in FIG. 9. In the present implementation, each housing portion 904, 906 includes a diagonally oriented recess 922 and a set of posts 924 to locate and hold the corresponding fluid filter 914. Also in the present implementation, the first port 314 and the second port 322 are oriented orthogonal to each other, and the third port 330 and the fourth port 334 are likewise oriented orthogonal to each other, with the first port 314 being proximal to the fourth port 334 and the second port 322 being proximal to the third port 330. Accordingly, the fluid flow through the inlet chamber 306 changes direction at the fluid filter 914, and the fluid flow through the outlet chamber 308 likewise changes direction at the fluid filter 914.

Also in the present implementation, the first housing portion 904 faces the main PCB 516 (FIG. 5). The first housing portion 904 includes two cut-outs (or openings) 932, 934. The temperature sensor 348 and the RH sensor 350 are collocated on the main PCB 516 with the respective cut-outs 932, 934, whereby the temperature sensor 348 and RH sensor 350 may protrude into the inlet chamber 306 or at least be exposed to the fluid flowing therethrough, upstream of the pump 116. Seals (not shown) may be provided at the interface between the temperature sensor 348 and RH sensor 350 and the cut-outs 932, 934 to minimize fluid loss from the inlet chamber 306. It will be noted that the second housing portion 906 may also nominally include the same cut-outs for purposes of lowering manufacturing costs. These cut-outs (if present) may be blocked by plugs, covered by tape, or otherwise sealed to prevent fluid loss from the outlet chamber 308.

In some implementations, the exhaust tube 336 has a length ranging from 1 to 15 cm, and an inside diameter ranging from 1 to 3 mm. The dimensions of the exhaust tube 336 may influence the effectiveness of the noise dampening provided by the noise dampening device 304, as discussed below.

In one evaluation of the aerosol exposure monitor 500 illustrated in FIGS. 5-10, the total sound level at one meter away from the aerosol exposure monitor 500 during operation of the pump 116 at a flow rate of 0.5 liters/minute was found to be 38 dBA (decibels, A-weighting), which is not much higher (less than 3 dBA higher) than the typical background sound level contemplated for a user. Therefore, the aerosol exposure monitor 500 may be characterized as being very quiet in operation, which is expected to promote wearing compliance by the user. FIG. 11 is a plot of measured sound level (dBA) of the aerosol exposure monitor 500 as a function of the length (cm) of the exhaust tube 336 of the noise dampening device 304, for a flow rate of 0.5 liters/minute. For comparison, a data point is also shown for the sound level when the aerosol exposure monitor 500 is operated without the noise dampening device 304. FIG. 11 demonstrates a significant reduction in sound level when the noise dampening device 304 is employed, with a noise level of only 1 dBA or less above ambient being attainable. As noted earlier in this disclosure, it has been found that children are not comfortable with sensor systems that add more than 5 decibels to the environment. By comparison, it can be seen that the aerosol exposure monitor 500 when provided with the noise dampening device 304 may be operated at a noise level well below (by a factor of two or more) the noise level found objectionable by children. FIG. 11 also demonstrates that noise dampening may be optimized through selection of an appropriate length for the exhaust tube 336.

In some implementations, the aerosol exposure monitor 500 (or 300) is configured to utilize the accelerometer data to calculate (or estimate, or predict) the ventilation rate ($m^3$/min, or liters/min) of the wearer during the sampling period. A strong correlation (e.g., $R^2$=0.90) has been found between accelerometer data and ventilation rate. In some implementations, the aerosol exposure monitor 500 is configured to utilize the accelerometer data to calculate (or estimate, or predict) the potential dose (µg/min/kg, where kg is the unit of body weight of the wearer) to which the wearer was exposed during the sampling period. In some implementations, the aerosol exposure monitor 500 is configured to utilize the nephelometer data ($\mu g/m^3$) in conjunction with the accelerometer data to make these calculations. FIG. 12 is a functional diagram illustrating examples of processes for calculating ventilation rate and potential dose. These calculations may be made, for example, in accordance with an algorithm executed by hardware and/or software of the aerosol exposure monitor 500.

Figure 13A:
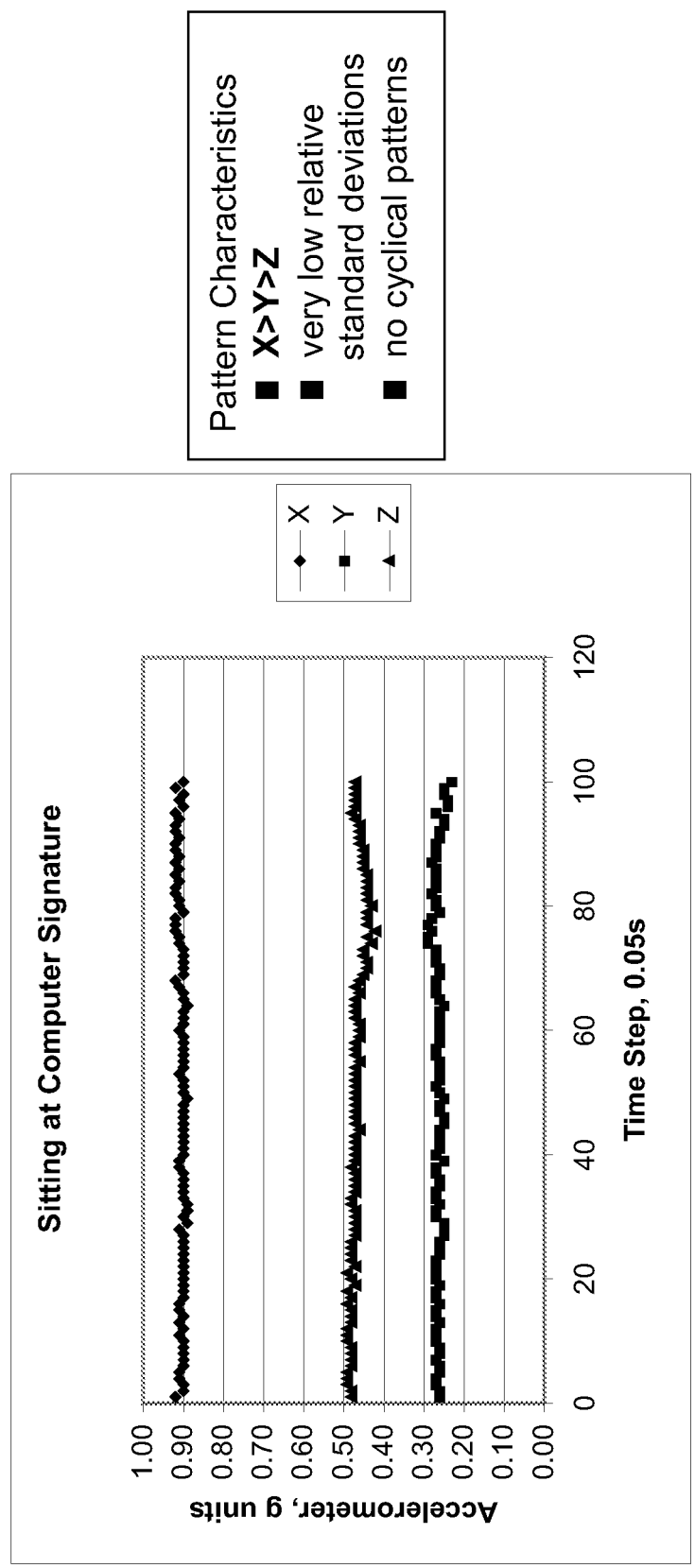
Figure 13B:
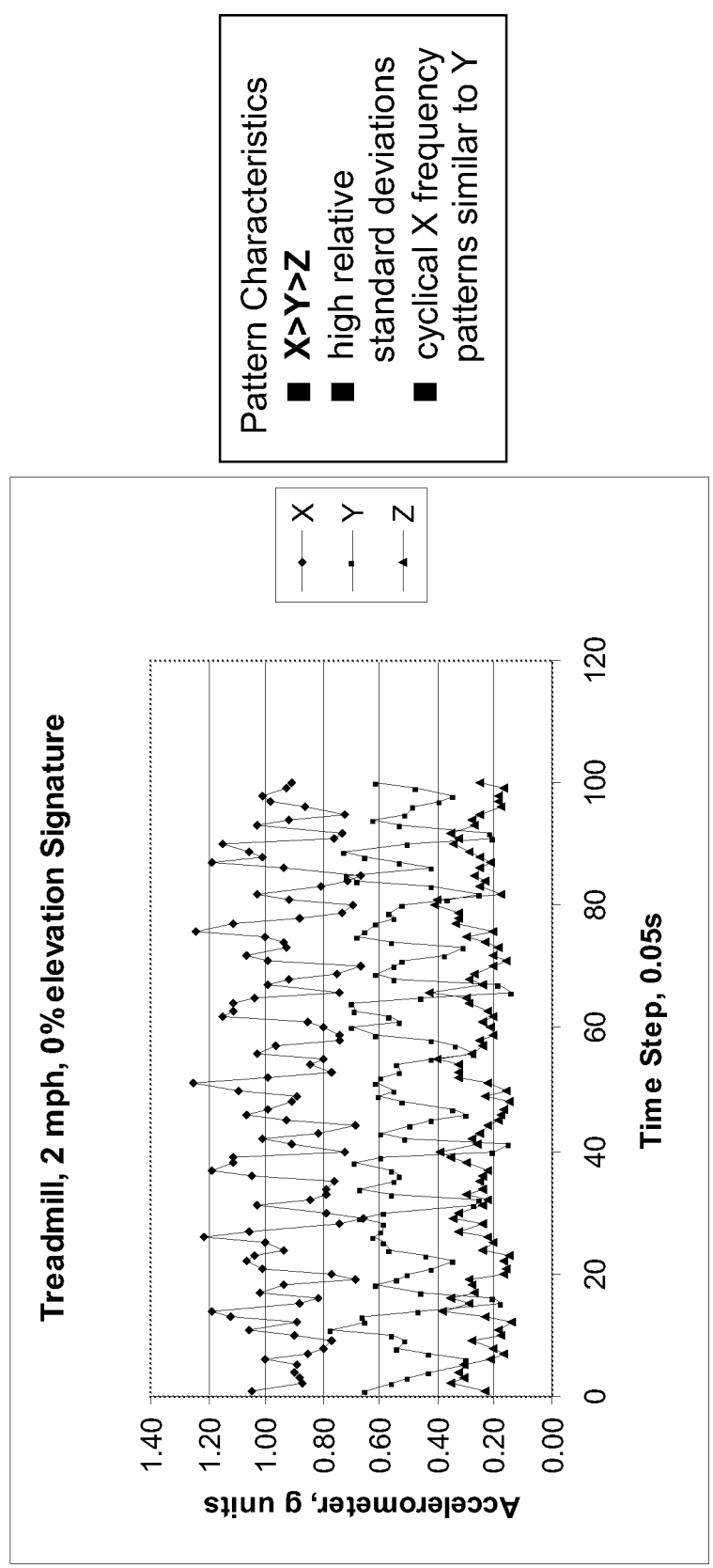
Figure 13C:
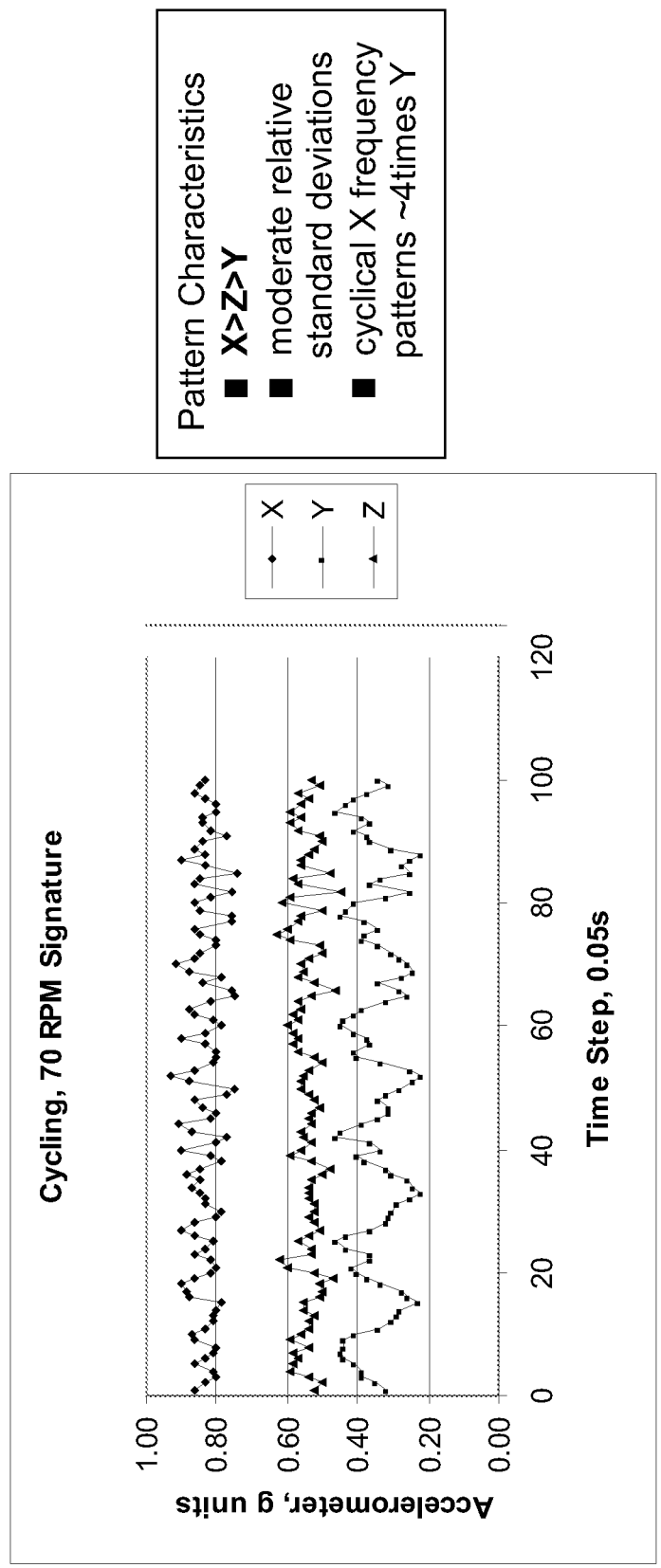

FIG. 13 are plots of raw tri-axial (x, y and z values) accelerometer data (in g units) over time (in sec) acquired from an accelerometer-equipped aerosol exposure monitor worn by a person while (A) sitting at a computer, (B) walking at 2 mph on a treadmill, and (C) indoor cycling at 70 RPM. The data were collected at a rate of 20 Hz, for five-second periods (a total of one hundred 0.05 s time steps). As evident from the plots of the more energetic activities (B and C) the accelerometer data exhibit distinctive patterns which, when combined with the signal resolution (about 0.02 g) of the accelerometer, may be utilized to identify the specific types of activity engaged in by the person while wearing the aerosol exposure monitor and the aerosol exposure monitor is being operated to acquire particle exposure-related data. As noted above, the acquisition, storage and optional processing of both the accelerometer data and the exposure data may be performed on-board the aerosol exposure monitor. It can be seen that the accelerometer data is acquired transparently to the person wearing the aerosol exposure monitor, and thus the person is not required to maintain time-activity diaries.

Figure 14:
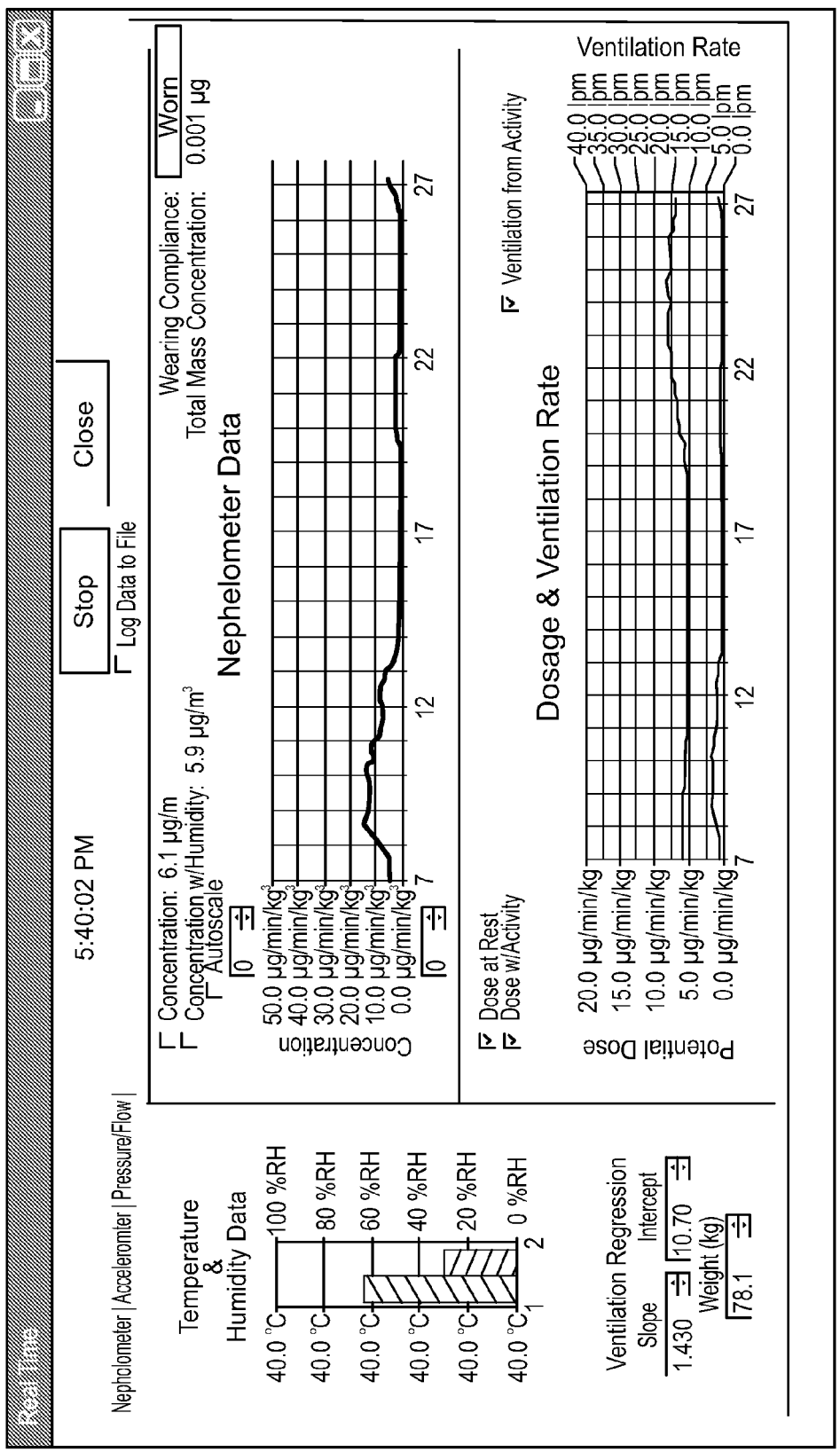

FIG. 14 is an example of a screenshot generated by software configured to provide an interface with the aerosol exposure monitor, typically between sampling periods (e.g., when the aerosol exposure monitor is not being worn by a user during a sampling period in the case of a personal exposure monitor). For example, the software may reside in and be executed by a computing device. After the completion of a sampling period, the aerosol exposure monitor may be placed in communication with the computing device, such as via a USB interface for example, and all data acquired by aerosol exposure monitor may be uploaded to the computer device for use by the software. As shown in FIG. 14, the software may be configured to merge the real-time concentration data with real-time estimates of the ventilation rate to output potential dose levels in µg/min/kg. As also shown, other types of data acquired from the aerosol exposure monitor may be concurrently presented such as, for example, temperature, relative humidity, wearing compliance level indication (e.g., worn, not worn), the body weight of the wearer, etc. As also shown, in addition to the "Nephelometer" other tabs providing displays of other types of the data may be included, such as an "Accelerometer" tab at which data similar to that shown in FIG. 13 may be presented, and a "Pressure/Flow" tab at which data acquired by on-board pressure sensors (such as described above), mass or volumetric flow sensors, or the like may be presented.

In general, terms such as "communicate" and "in . . . communication with" (for example, a first component "communicates with" or "is in communication with" a second component) are used herein to indicate a structural, functional, mechanical, electrical, signal, optical, magnetic, electromagnetic, ionic or fluidic relationship between two or more components or elements. As such, the fact that one component is said to communicate with a second component is not intended to exclude the possibility that additional components may be present between, and/or operatively associated or engaged with, the first and second components.

It will be understood that various aspects or details of the invention may be changed without departing from the scope of the invention. Furthermore, the foregoing description is for the purpose of illustration only, and not for the purpose of limitation—the invention being defined by the claims.

What is claimed is:

1. An aerosol exposure monitor, comprising:
an impactor;
a sample chamber communicating with the impactor and defining a laminar fluid flow path along a first axis;
a collection filter communicating with the sample chamber and removable from the aerosol exposure monitor;
a pump communicating with the collection filter;
a light source configured to generate a light beam that occupies a sensing volume in the sample chamber, wherein the fluid flow path passes through the sensing volume along the first axis, and the light beam propagates along a second axis that is at an angle to the first axis;
a light detector;
a first bore defining a first optical path from the light source to the sensing volume along the second axis; and
a second bore defining a second optical path from the sensing volume to the light detector along a third axis, wherein the first axis, the second axis and the third axis are at angles to each other.

2. The aerosol exposure monitor of claim 1, comprising at least one of the following:
a sample inlet comprising an inlet opening configured such that the sample inlet establishes an inlet flow path that turns ninety degrees from the inlet opening to the impactor;
a light trap disposed on a side of the sample chamber opposite to the first bore;
an accelerometer configured for detecting motion of the aerosol exposure monitor along one or more axes;
a differential pressure sensor configured for detecting a pressure drop across an orifice between the collection filter and the pump;
a differential pressure sensor configured for detecting a pressure drop between an inlet side of the impactor and an outlet side of the collection filter.

3. The aerosol exposure monitor of claim 1, wherein the impactor comprises a plurality of impactor stages, each successive impactor stage having a smaller cut-point than the other impactor stages.

4. The aerosol exposure monitor of claim 1, wherein the sample chamber has a length between the impactor and the collection filter ranging from 20 mm to 22 mm, and a cross-sectional dimension ranging from 9 mm to 14.5 mm.

5. The aerosol exposure monitor of claim 1, wherein the pump is configured for providing a flow rate ranging from 0.30 to 0.60 liters per minute.

6. The aerosol exposure monitor of claim 1, wherein the light source is configured according to at least one of the following:
the sensing volume is cylindrical;
the sensing volume is cylindrical, and has a length ranging from 8.0 to 12.0 mm and a diameter ranging from 0.5 to 2.0 mm;
the sensing volume is an elliptic cylinder.

7. The aerosol exposure monitor of claim 1, wherein the light detector comprises a rectilinear sensing area communicating with the second bore.

8. The aerosol exposure monitor of claim 1, comprising electronic circuitry configured according to at least one of the following:
- electronic circuitry configured for collecting quality control data during operation of the aerosol exposure monitor;
- electronic circuitry configured for collecting quality control data during operation of the aerosol exposure monitor, wherein the quality control data are selected from the group consisting of a flow rate of fluid through the collection filter, a pressure drop through the collection filter, a pressure drop from an inlet side of the impactor to an outlet side of the collection filter, a temperature of fluid flowing through the aerosol exposure monitor, a relative humidity of fluid flowing through the aerosol exposure monitor, data produced by an accelerometer of the aerosol exposure monitor defining wearing compliance, a voltage level of a battery of the aerosol exposure monitor, GPS data pertaining to a location of the aerosol exposure monitor, and a combination of two or more of the foregoing;
- electronic circuitry configured for adjusting the pump based on a parameter selected from the group consisting of a flow rate of fluid through the collection filter, a pressure drop across an orifice following the collection filter, a pressure drop from an inlet side of the impactor to an outlet side of the collection filter, a temperature of fluid flowing through the aerosol exposure monitor, a relative humidity of fluid flowing through the aerosol exposure monitor, and a combination of two or more of the foregoing.

9. The aerosol exposure monitor of claim 1, comprising at least one of the following:
- a noise dampening device communicating with the pump;
- a noise dampening device communicating with the pump, wherein the noise dampening device comprises an inlet chamber, an outlet chamber, and an elastomeric membrane interposed between and fluidly isolating the inlet chamber and the outlet chamber, wherein the inlet chamber is interposed between the collection filter and the pump inlet, and the outlet chamber communicates with the pump outlet.

10. A method for monitoring aerosol, the method comprising:
- sizing particles of the aerosol by flowing the aerosol through an impactor;
- collecting the sized particles by flowing the aerosol through a sample chamber along a first axis and through a collection filter, wherein the sized particles are collected on the collection filter, and wherein flowing the aerosol through the impactor, the sample chamber and the collection filter comprises operating a pump communicating with an outlet side of the collection filter;
- irradiating the sized particles flowing through the sample chamber by directing an irradiating light into the sample chamber along a second axis angled relative to the first axis, wherein the irradiating light establishes a sensing volume in the sample chamber, the aerosol flows through the sensing volume along the first axis, and scattered light propagates from the irradiated particles;
- directing the scattered light from the sensing volume to a light detector along a third axis angled relative to the first axis and the second axis to sense a total scattering potential of the sized particles; and
- a light source configured to generate a light beam that occupies a sensing volume in the sample chamber, wherein the fluid flow path passes through the sensing volume along the first axis, and the light beam propagates along a second axis that is at an angle to the first axis.

11. The method of claim 10, comprising at least one of the following:
- wherein the flow of aerosol out from the impactor, through the sample chamber, and to the collection filter is substantially laminar;
- wherein the aerosol is flowed through the collection filter at a total system pressure drop through the collection filter of 2 inches $H_2O$ or less;
- wherein the aerosol is flowed through the collection filter at a flow rate ranging from 0.30 to 0.60 liters/min.

12. The method of claim 10, wherein directing the irradiating light into the sample chamber comprises at least one of the following:
- establishing a cylindrical sensing volume of light in the sample chamber;
- establishing a cylindrical sensing volume of light in the sample chamber, and the cylindrical sensing volume has a length ranging from 8.0 to 12.0 mm and a cross-sectional dimension ranging from 0.5 to 2.0 mm;
- establishing a cylindrical sensing volume of light in the sample chamber, wherein the cylindrical sensing volume has an elliptical cross-section and the cross-sectional dimension is a major axis.

13. The method of claim 10, wherein directing the scattered light to the light detector comprises directing the scattered light from the sample chamber as a beam having a rectilinear cross-section.

14. The method of claim 10, comprising acquiring particle concentration data from the light detector, and subjecting the collection filter to a particle analysis.

15. The method of claim 10, comprising at least one of the following:
- operating an aerosol exposure monitor to size the particles, collect the sized particles, irradiate the sized particles and direct the scattered light, while a user is wearing the aerosol exposure monitor;
- operating an aerosol exposure monitor to size the particles, collect the sized particles, irradiate the sized particles and direct the scattered light, while a user is wearing the aerosol exposure monitor, and acquiring accelerometer data corresponding to movement of the user while wearing the aerosol exposure monitor to provide an indication of activity of the user during wearing of the aerosol exposure monitor near a breathing zone of the user;
- operating an aerosol exposure monitor to size the particles, collect the sized particles, irradiate the sized particles and direct the scattered light, while a user is wearing the aerosol exposure monitor, and acquiring accelerometer data corresponding to movement of the user while wearing the aerosol exposure monitor to provide an indication of activity of the user during wearing of the aerosol exposure monitor near a breathing zone of the user, and calculating a ventilation rate ($m^3$/min) of the user during wearing of the aerosol exposure monitor based on the accelerometer data, calculating a potential dose (µg/min/kg) of the user during wearing of the aerosol exposure monitor based on the accelerometer data and on particle concentration data acquired from the light detector, or calculating both the ventilation rate and the potential dose.

* * * * *